(12) United States Patent
Ahluwalia et al.

(10) Patent No.: US 11,510,700 B2
(45) Date of Patent: Nov. 29, 2022

(54) SYSTEMS AND METHODS FOR A DYNAMIC MEDICAL HOLDER

(71) Applicants: Prabhat Kumar Ahluwalia, Little Falls, NY (US); Puja Ahluwalia, Little Falls, NY (US)

(72) Inventors: Prabhat Kumar Ahluwalia, Little Falls, NY (US); Puja Ahluwalia, Little Falls, NY (US)

(*) Notice: Subject to any disclaimer, the term of this patent is extended or adjusted under 35 U.S.C. 154(b) by 0 days.

(21) Appl. No.: 17/315,445

(22) Filed: May 10, 2021

(65) Prior Publication Data

US 2021/0259741 A1    Aug. 26, 2021

Related U.S. Application Data

(63) Continuation of application No. 16/513,915, filed on Jul. 17, 2019, now abandoned, which is a continuation of application No. 15/673,068, filed on Aug. 9, 2017, now Pat. No. 10,413,327, which is a continuation of application No. PCT/US2016/018448, filed on Feb. 18, 2016.

(60) Provisional application No. 62/117,524, filed on Feb. 18, 2015.

(51) Int. Cl.
  *A61B 17/42*    (2006.01)
  *A61B 90/50*    (2016.01)
  *A61B 46/23*    (2016.01)
  *A61B 17/00*    (2006.01)

(52) U.S. Cl.
  CPC .......... *A61B 17/4241* (2013.01); *A61B 17/42* (2013.01); *A61B 46/23* (2016.02); *A61B 90/50* (2016.02); *A61B 2017/00455* (2013.01); *A61B 2017/4216* (2013.01)

(58) Field of Classification Search
  CPC ..... A61B 17/4241; A61B 46/23; A61B 90/50; A61B 17/42; A61B 2017/00455; A61B 2017/4216
  USPC ....... 248/128, 139, 151, 393, 397, 419, 424, 248/287.1, 298.1; 606/119
  See application file for complete search history.

(56) References Cited

U.S. PATENT DOCUMENTS

| | | | | |
|---|---|---|---|---|
| 1,622,847 | A * | 3/1927 | Rundgren | A47B 27/02 248/397 |
| 9,615,733 | B2 * | 4/2017 | Nottmeier | A61B 90/50 |
| 2009/0287062 | A1 * | 11/2009 | Farley | A61B 17/0206 600/231 |
| 2010/0108841 | A1 * | 5/2010 | Kronner | A61B 90/50 248/228.4 |
| 2010/0160928 | A1 * | 6/2010 | Navas | A61B 17/4241 606/119 |
| 2014/0276916 | A1 * | 9/2014 | Ahluwalia | A61B 90/50 606/119 |
| 2015/0133958 | A1 * | 5/2015 | Singh | A61B 90/50 606/130 |
| 2017/0340353 | A1 * | 11/2017 | Ahluwalia | A61B 46/23 |

(Continued)

*Primary Examiner* — Muhammad Ijaz
(74) *Attorney, Agent, or Firm* — Pierson IP, PLLC

(57) ABSTRACT

Embodiments systems and methods for a platform that is configured to hold a medical device. In embodiments, a physician, nurse, medical practitioner, etc. may perform actions to change the positioning and orientation of the medical device while the medical device is secured to the platform. In further embodiments, the platform may include robotic components configured to change the positioning and orientation of the medical device.

19 Claims, 31 Drawing Sheets

(56) References Cited

U.S. PATENT DOCUMENTS

2018/0028387 A1* 2/2018 Yellin .................... A61B 34/70

* cited by examiner

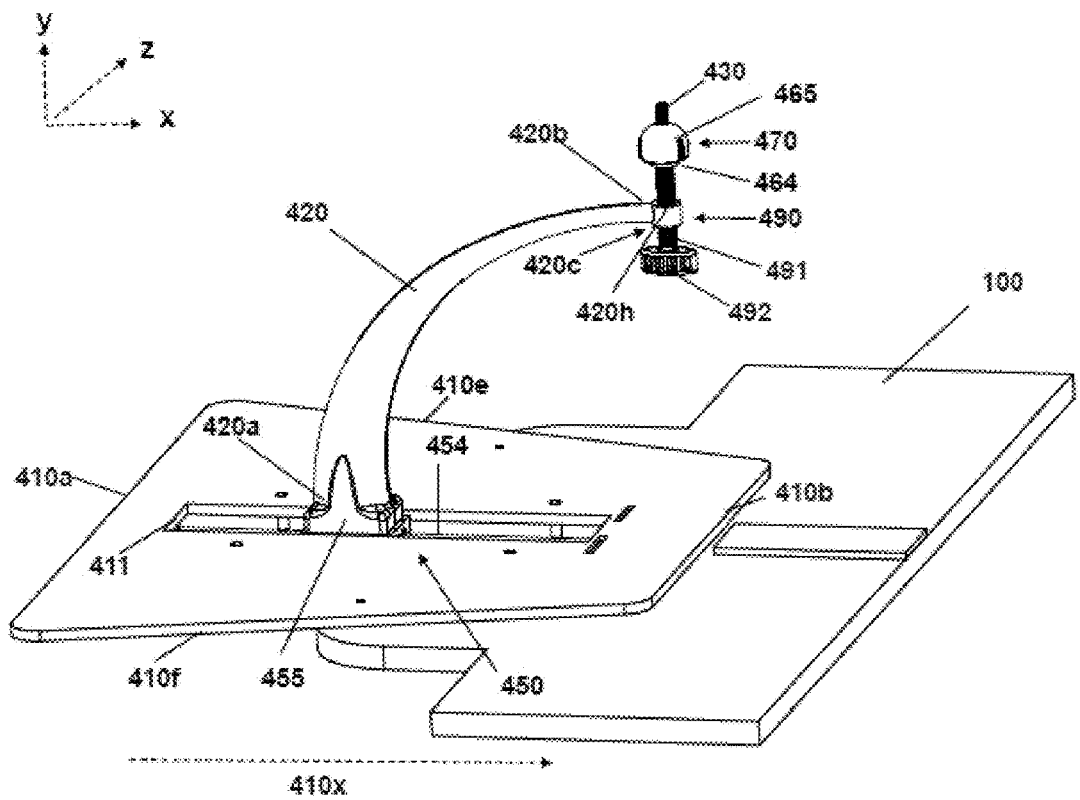
FIG 1D
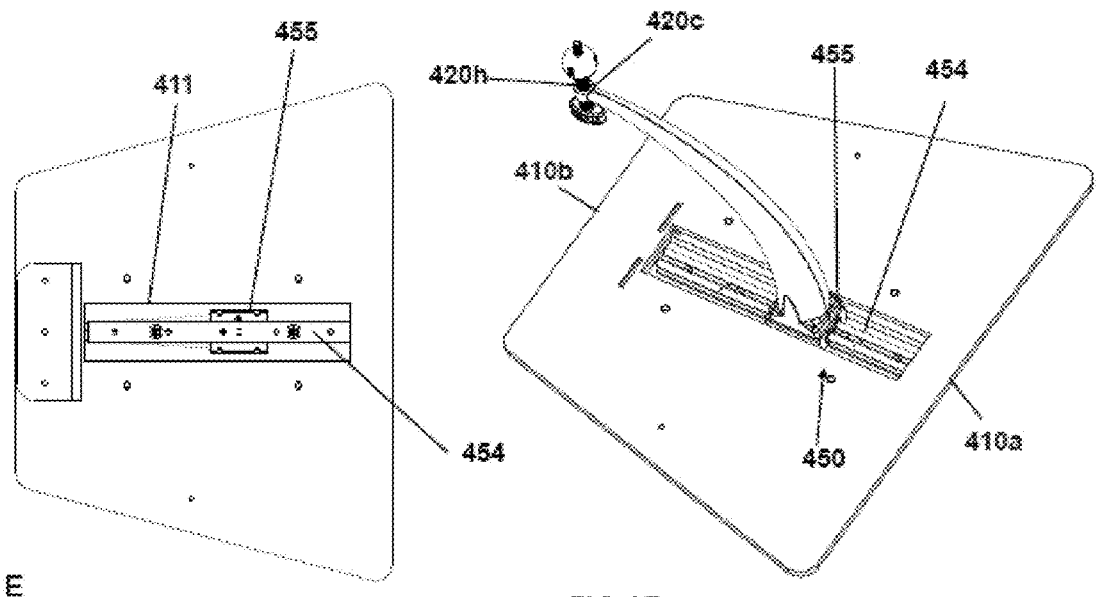
FIG 1E
FIG 1F

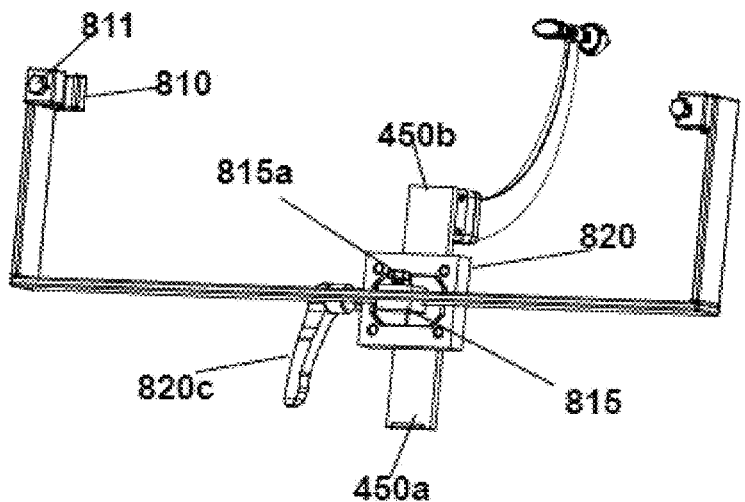
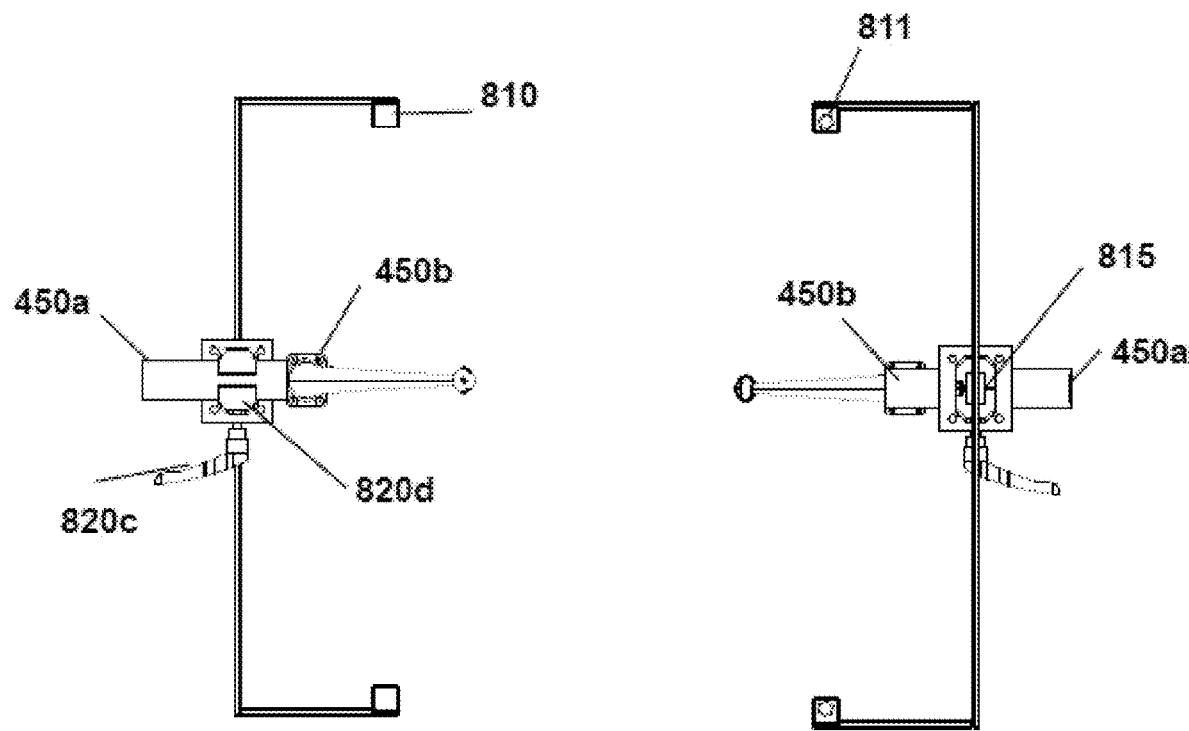

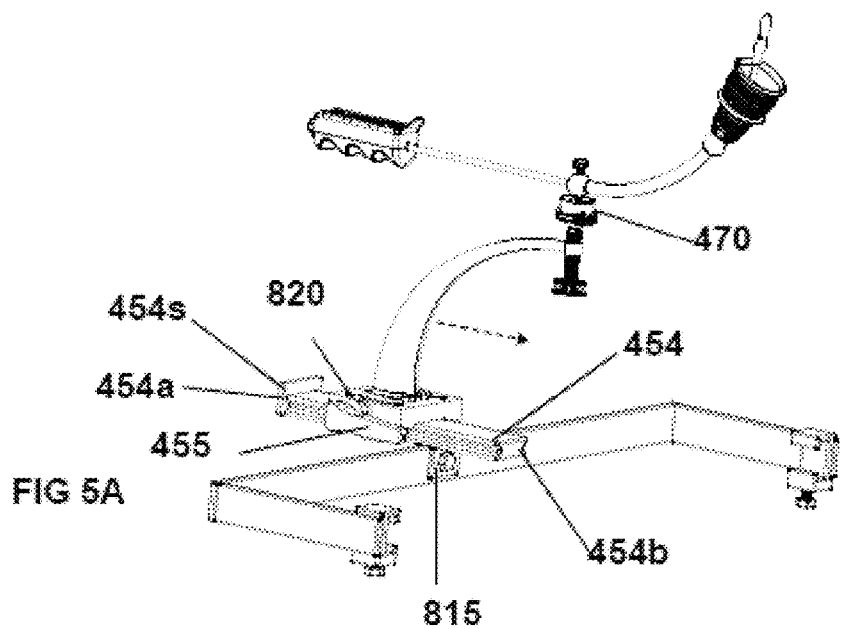
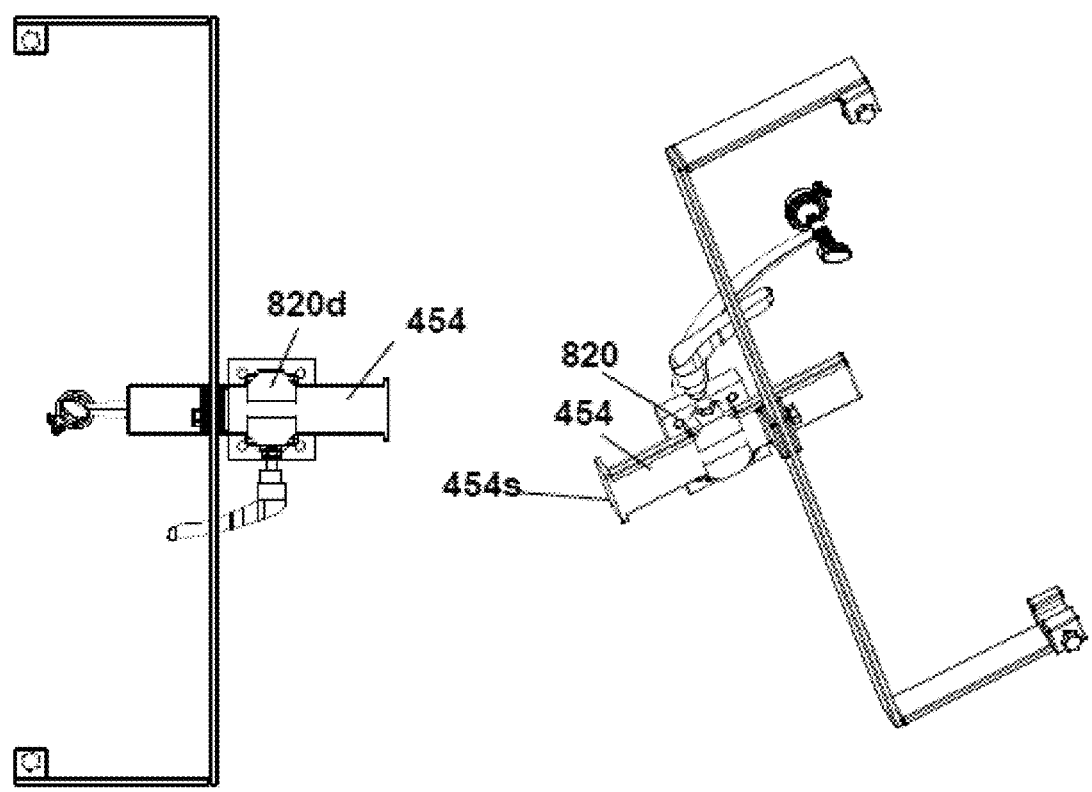

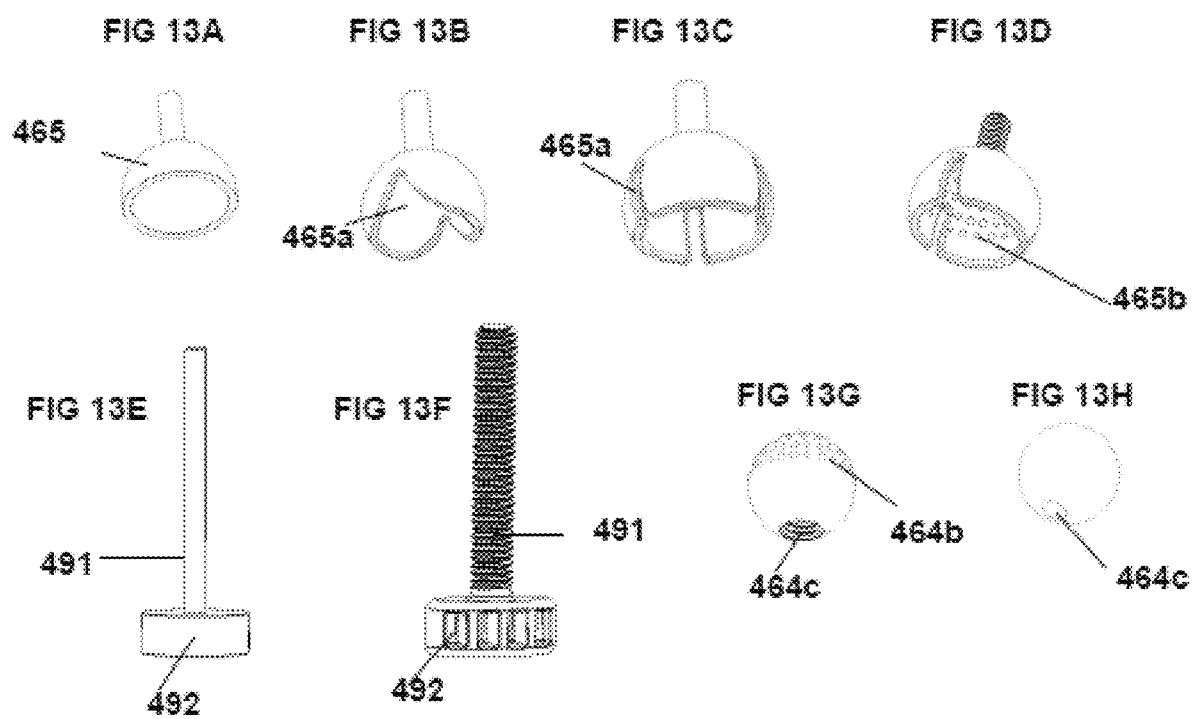

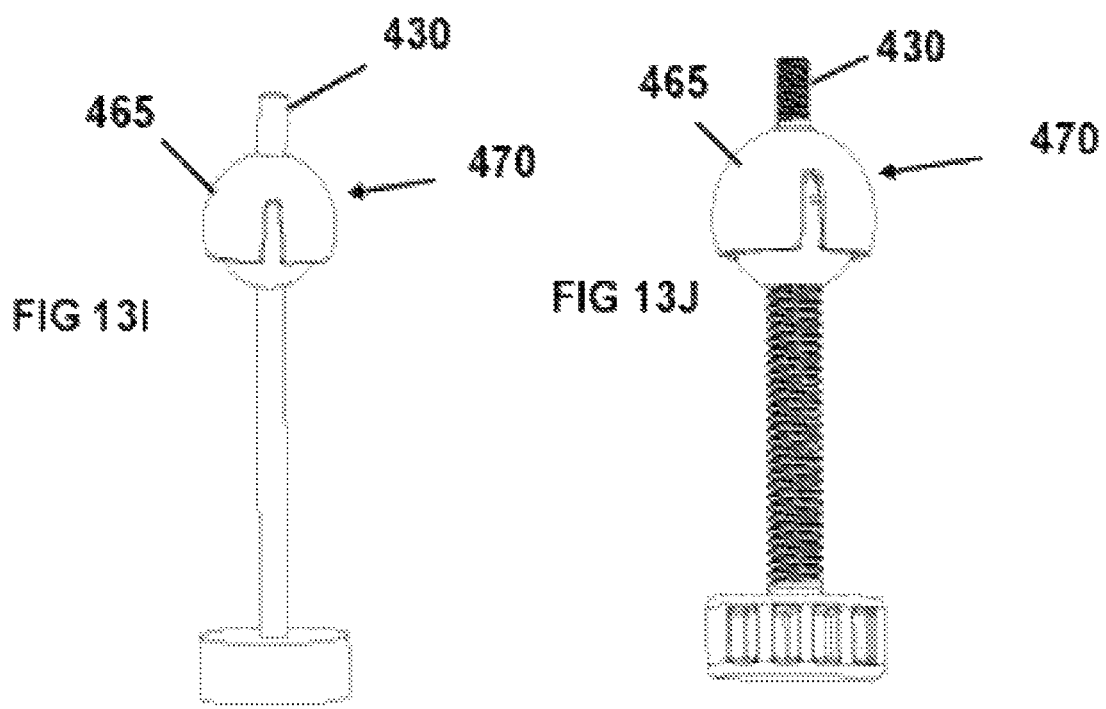

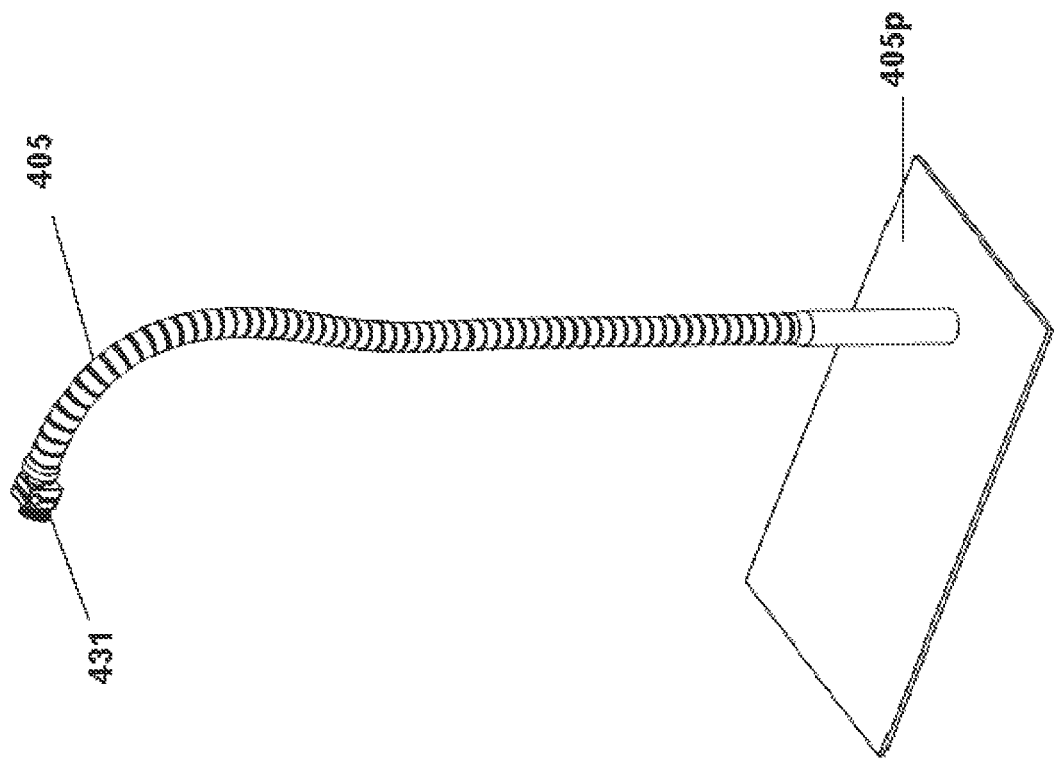

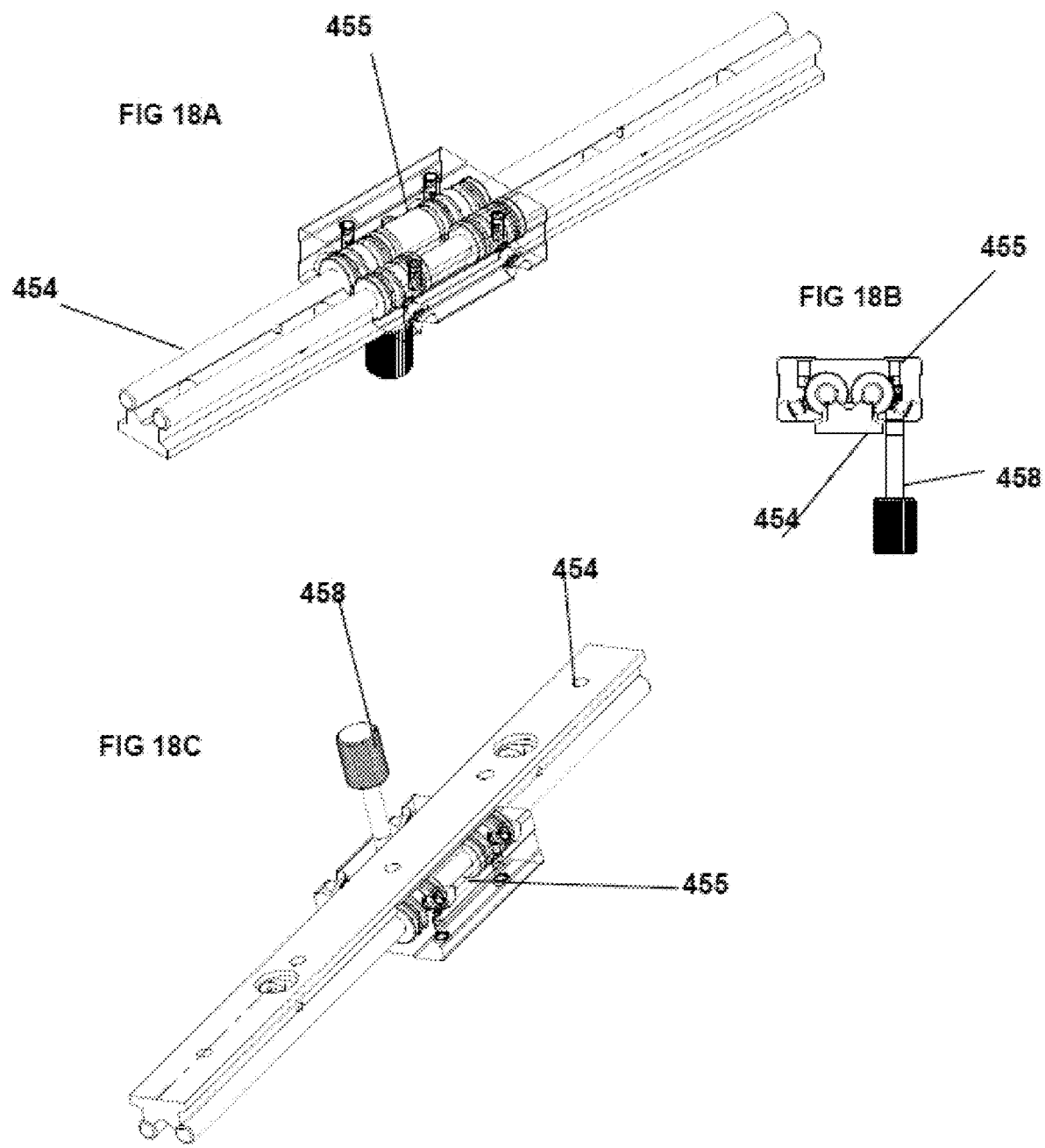

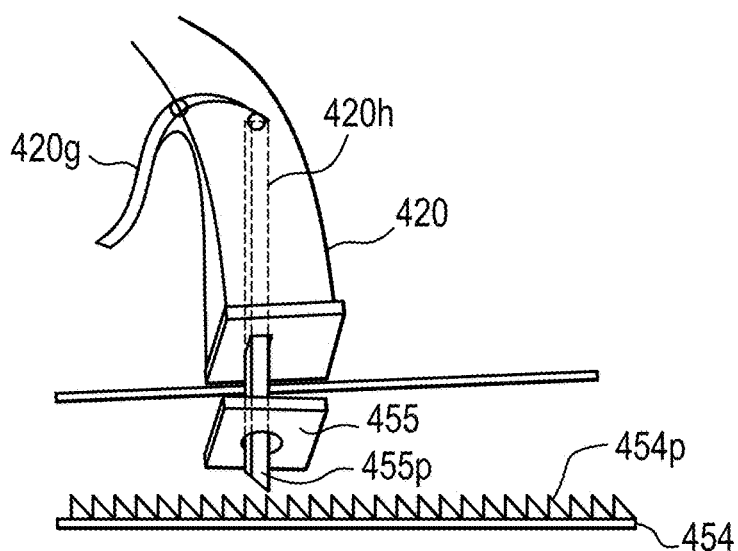
FIG. 21C
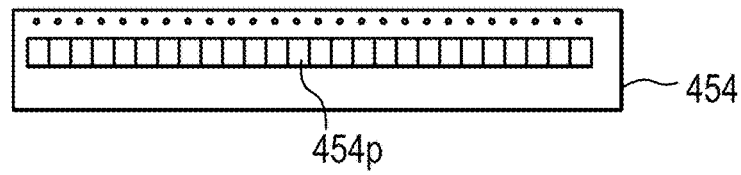
FIG. 21D
FIG. 21E
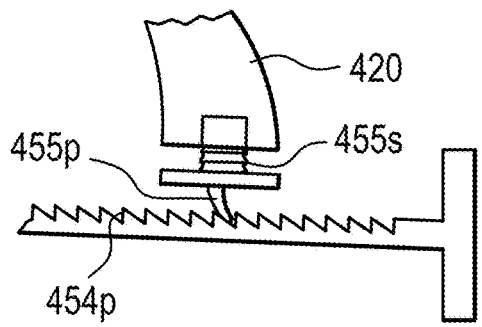
FIG. 21G
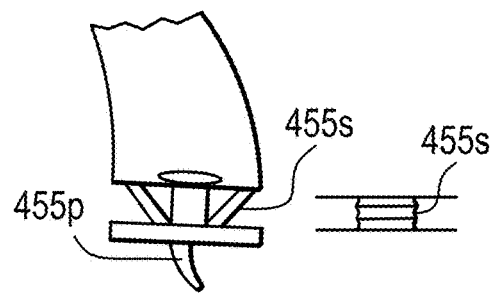
FIG. 21F
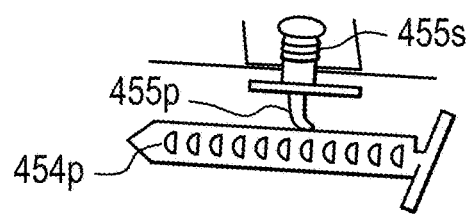

SYSTEMS AND METHODS FOR A DYNAMIC MEDICAL HOLDER

CROSS-REFERENCE TO RELATED APPLICATIONS

This application claims a benefit of priority under 35 U.S.C. § 119 to U.S. Provisional Patent Application No. 62/117,524 filed Feb. 18, 2015 and PCT/US16/18448 filed Feb. 18, 2016, which are hereby fully incorporated herein by reference in its entirety.

BACKGROUND INFORMATION

Field of the Disclosure

Examples of the present disclosure are related to systems and methods for a dynamic manipulator, uterine manipulator, surgical instrument, or vaginal instrument holder (hereinafter "holder"). More particularly, embodiments relate to coupling a holder to an end of an operating table or surgical platform, wherein the holder may slide along a track.

Background

While performing a hysterectomy or other surgical procedures on a woman, it may be required that the woman's uterus is manipulated, such that a physician may view the uterus and cervix properly. For example, when performing a hysterectomy, the woman's uterus may be manipulated to view portions of the uterus to surgically remove the uterus, cervix, ovaries, fallopian, tube, and other surrounding bodily structures.

Conventionally, when performing a surgical procedure on a woman, the woman may be required to lie down on an operating table, and a nurse is required to physically hold a manipulator during the duration of the surgical procedure. However, the surgical procedure may take several hours, and thus unduly burdensome for the nurse to physically hold the manipulator during the entire surgical procedure.

Furthermore, during the surgical procedure, the physician is required to instruct the nurse to change the orientation of the manipulator, such as the direction and angle of the manipulator. Even with proper instructions, it is difficult to move the manipulator in the exact direction and angle desired by the physician.

Accordingly, needs exist for more effective and efficient systems and methods for a medical device configured to hold a manipulator, wherein the positioning and orientation of the manipulator is configured to change while being secured to a platform.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

FIGS. 1A-1F illustrate embodiments of a medical device holder, operating table attachment, coupling mechanism configured to couple to a medical device and the base portion of an operating table, thereby enabling stable, secure and precise use of device through a medical procedure.

FIGS. 4A-4E illustrate an alternative embodiment, wherein a holder is configured to couple to a device and the side-rails or extended protrusions of an operating table.

FIG. 5A-5C illustrates a perspective, top and bottom views respectively of a similar embodiment as FIG. 4A.

FIGS. 13A-13D show perspective views of various embodiments of various sockets or caps for a ball-and-socket rotational translator.

FIG. 13E shows an embodiment of a shaft and base, which may be compatible with a various embodiments of rotational translators.

FIG. 13F shows an embodiment of a threaded shaft and base configured for a screw designed vertical translator.

FIG. 13G shows an embodiment of an outer texture surface of a cap.

FIG. 13H shows an embodiment of an outer surface of a cap, wherein the outer surface of the cap is smooth.

FIGS. 13I and 13J show embodiments of a ball-and-socket rotational translator.

FIG. 17 shows an embodiment of gooseneck arm as a rotational, vertical, or horizontal translator.

FIGS. 18A-18C show respective perspective, side and bottom perspective views of a rail.

FIG. 21C shows a side perspective view of an embodiment longitudinal translator.

FIG. 21D shows a top view of a rail with a series of valleys.

FIG. 21E shows a side view of an embodiment wherein a pin is spring-loaded via a spring pin or spring.

FIG. 21F shows a perspective view of FIG. 21E.

FIG. 21G shows alternative embodiment of a spring.

Figure 1A:
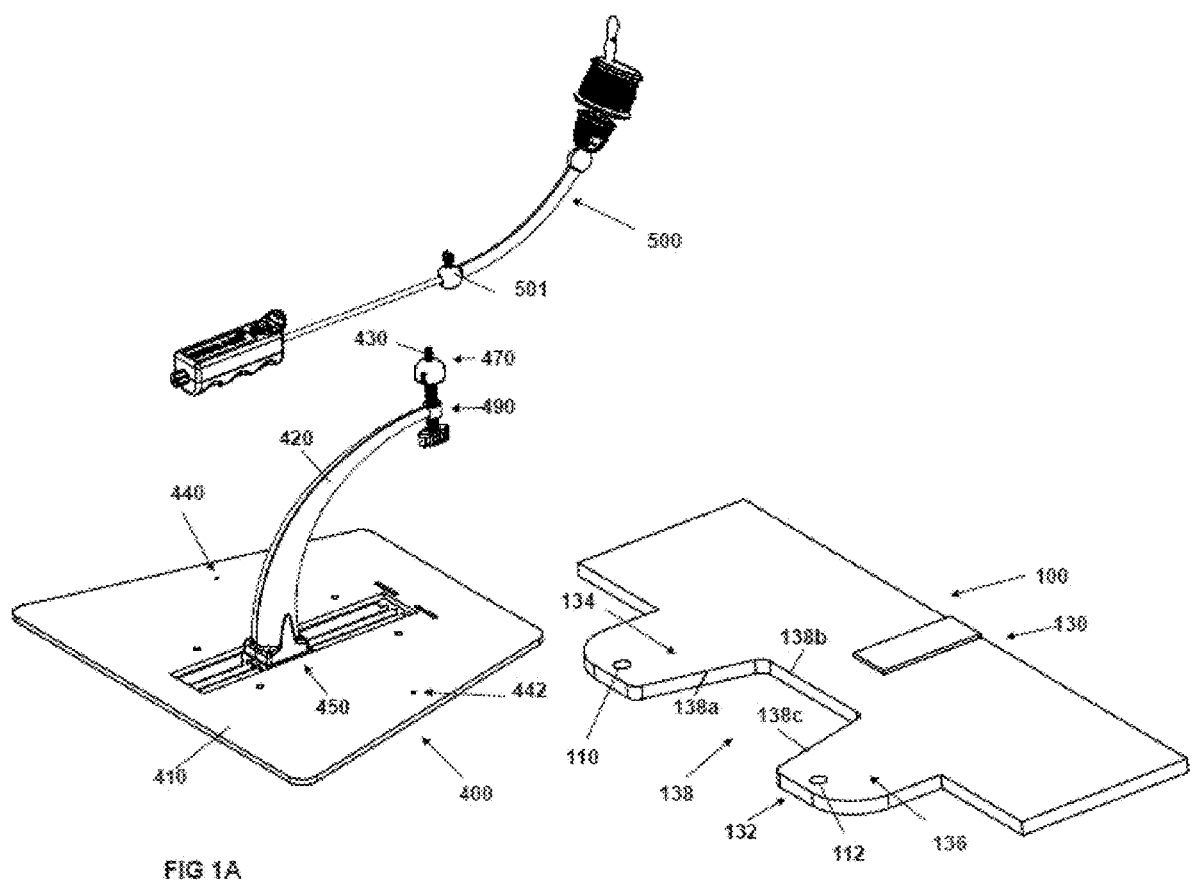

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present disclosure. Also, common but well-understood elements that are useful or necessary in a commercially feasible embodiment are often not depicted in order to facilitate a less obstructed view of these various embodiments of the present disclosure.

DETAILED DESCRIPTION

In the following description, numerous specific details are set forth in order to provide a thorough understanding of the present embodiments. It will be apparent, however, to one having ordinary skill in the art that the specific detail need not be employed to practice the present embodiments. In other instances, well-known materials or methods have not been described in detail in order to avoid obscuring the present embodiments.

Embodiments describe systems and methods for a medical device that is configured to hold a manipulator. In embodiments, a physician, nurse, medical practitioner, etc. (referred to hereinafter collectively and individually as "physician") may perform actions to change the positioning and orientation of the manipulator while the manipulator is secured to a platform. In further embodiments, the medical device may include robotic components configured to change the positioning and orientation of the manipulator.

Throughout this specification, several elements will be described as being a "motion system" or part of a motion system; such systems include non-linear systems and linear systems, which may have components such as ball bearings, dovetail bearings, linear roller bearings, magnetic or fluid bearings, recirculating ball bearings, crossed roller bearings, flexures, cylindrical sleeves, linear ball bushings, guides, actuators, ways, machine slides, XY tables, roller tables and dovetail slides. These manual and motorized embodiments in addition to their braking systems are captured throughout this specification.

Specifically motion system may be described as having a "carriage", "rail" and/or "brake". "Carriage" may include ball, ball bearings, wheels, casters, grooves, or any feature to support motion. "Rail" may be comprised of one or more rails, channel, guiderails, groves, slides, gully, channels, tracks. In addition, "brake" may be comprised of bolts, screw, locks, fasteners, brakes, clips, clamps, pins, latches, pegs, or any other braking feature configured to apply friction.

FIGS. 1A-1F illustrate an embodiment of a medical device holder, operating table attachment, coupling mechanism 400 (hereinafter "holder 400") configured to couple to a medical device 500 (hereinafter "device 500") and the base portion 100 of an operating table (hereinafter "base 100"), thereby enabling stable, secure and precise use of device 500 through a medical procedure. In this embodiment and other embodiments throughout this specification, device 500 is shown as a uterine manipulator. However, one skilled in the art will appreciate that any other medical device that may be used in a medical environment, such as a hospital, and may be attached to holder 400 where the application is appropriate.

Figure 1B:
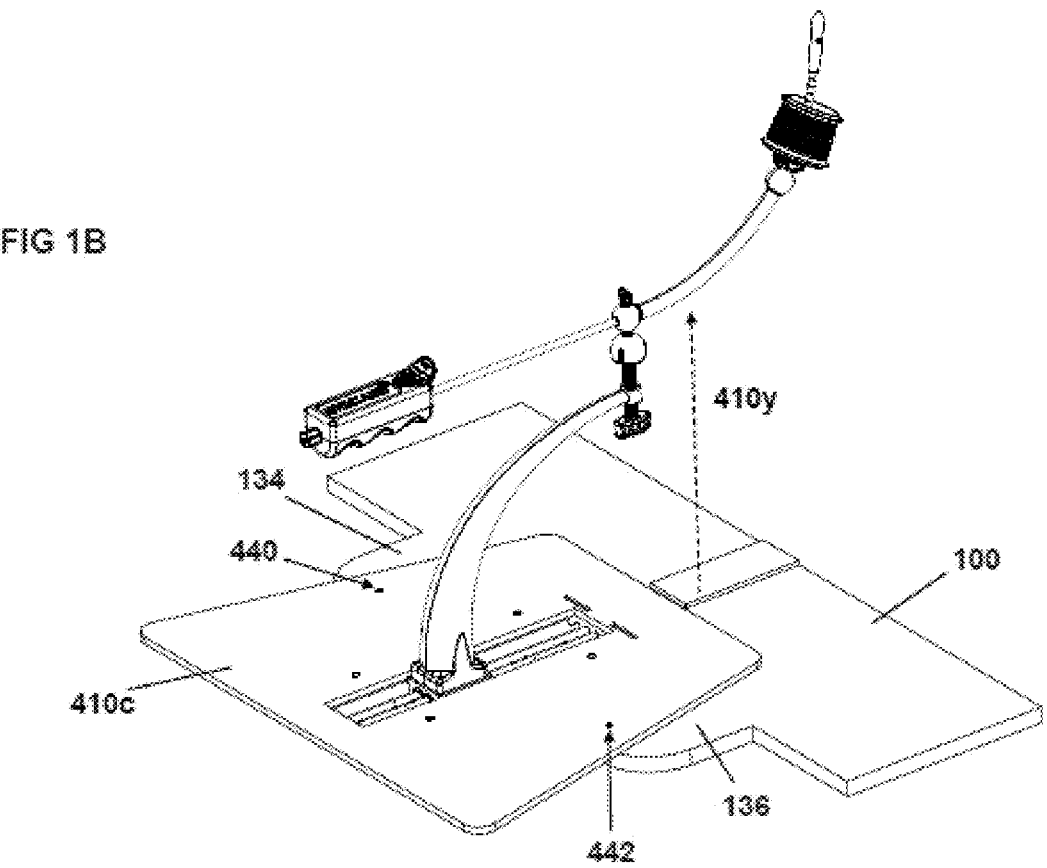
Figure 1C:
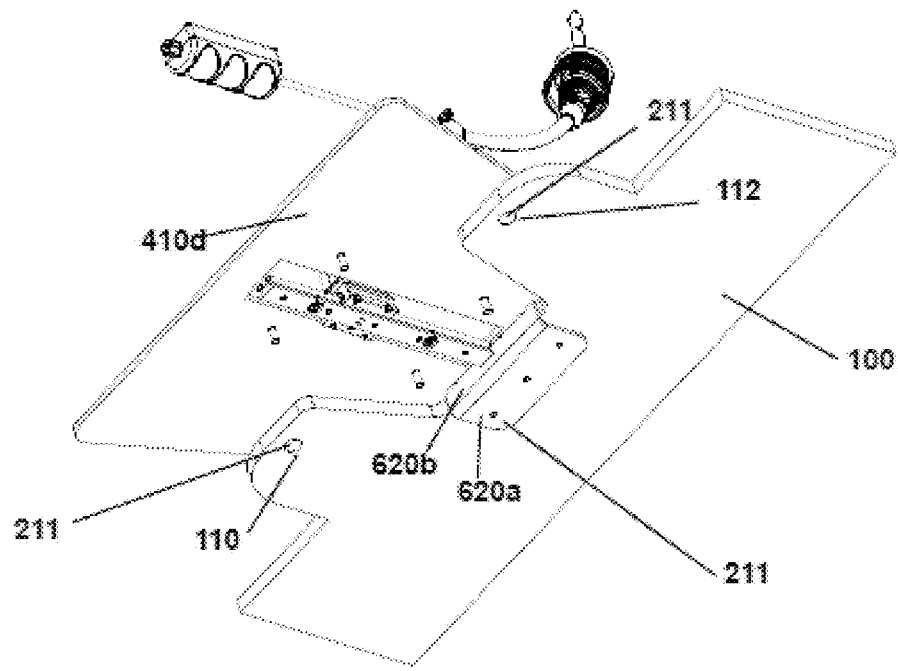

FIG. 1A illustrates a perspective view of an unassembled holder 400, device 500 and base 100. FIGS. 1B and 1C depict perspective views of an assembled holder 400, device 500, and base 100. One skilled in the art will appreciate that the elements in embodiments may be manufactured separately, or be combined in part or whole. For example, base 100 may be removable from or integral with the operating table. Device 500 may be integrated with holder 400 as one component. Holder 400 and base 100 may be integrated as one component.

FIG. 1A illustrates an embodiment of base 100 having a first end 130 and a second end 132, wherein the second end 132 may include a first projection, tab, etc. (hereinafter "projection 134"), a second, projection, tab, etc. 136 (hereinafter "projection 136"), and inlet, slot, or cavity 138 (hereinafter "cavity 138") between the projections with first edge 138a, second edge 138b, and third edge 138c. Base 100 also includes a first orifice 110 and a second orifice 112 positioned on projections 134 and 136, respectively. When a patient is positioned on the operating table, first projection 134 is configured to be aligned with a first leg of the patient, second projection 136 is configured to be aligned with a second leg of the patient, and the pelvic cavity is accessible via the cavity 138. Although cavity 138 is represented as a trapezoidal cutout in FIG. 1, one skilled in the art will appreciate that cavity 138 may be any desired shape and/or size.

Some operating tables may include two bases or base portions, vertically aligned. Descriptions of embodiments throughout this specification may be configured to attach to either or both base portions. One skilled in the ordinary art can appreciate variations in the embodiments described below to accommodate positioning a holder 400 on either base portion, in between the base portions, above or below the base portions.

As shown in FIG. 1A, holder 400 includes a plate 410 (hereinafter "plate 410"); longitudinal axis translator 450 (hereinafter "longitudinal translator 450") which translates along the X-axis; handle, mallet, stick, grip, shaft, or stem 420 (hereinafter "stem 420"), rotational translator 470, vertical translator 490 which translates along the y-axis, and device coupler 430.

Plate 410 may be a solid or hollow plate, board, or material with a top surface 410c and bottom surface 410d configured to support device 500 and couple to a base 100 of an operating table. In FIG. 1A, plate 410 is shown as having a trapezoidal shape. However, plate 410 may be any desired shape and/or size configured to slide into, couple to, or rest upon base 100. For example, plate 410 may also be polygonal, curved, or any other shape which allows integration into and with the base 100 and/or cavity 138. For example, plate may be cross shaped, or may include one or more pieces to enable attachment to base 100 or a base portion of an operating table, as for example shown in FIG. 27. Plate 410 may be convex or concave, for example to achieve a "caulking gun" like embodiment shown in FIG. 23. Plate 410 may be configured to cover the area defined by cavity 138 within base 100. Plate may partially or totally cover cavity 138. Plate 410 may be positioned over, under, or within cavity 138.

Plate 410 may also include coupling fixtures to secure it to base 100. As shown in FIG. 1A, plate 410 may include orifices (e.g., orifices 440 and 442) configured for receiving coupling mechanisms such as projections, bolts, screws, washers, fasteners, knobs, or other coupling mechanisms (referred to hereinafter collectively and individually as "bolts 211"). Responsive to inserting bolts 211 through orifices 440 and 442 and into orifices 110 and 112 positioned within base 100, plate 410 and base 100 may be coupled together. Experiments have shown that a distance between orifices 440 and 442 may be desirable to be between 8 to 11 inches to achieve stable coupling with the base portion of an operating table or base 100 in North America. Bolts 211 may be removable pieces or may be integral or a permanently coupled to plate 410 designed to couple, attach pass through, or snap into the base 100's orifices (e.g., orifices 110 and/or 112). Plate 410 may also include alternative coupling mechanisms, such as a lock, arm, or shelf that is configured to interface with the base 100.

FIGS. 1B and 1C depict top and bottom perspective views of an embodiment of the holder 400, device 500, and base 100 assembled. The assembled views show plate 410's orifices 440 and 442 positioned on top of base 100's orifices 110 and 112 respectively, and coupled by bolts 211.

FIG. 1C also illustrates a stabilizing wing, arm, cap, clamp, cover, or shelf 620 (hereinafter "shelf 620") against bottom surface 410d of the plate's second end 410b, configured to slide over, encapsulate, snap into or surround an edge of a base 100, or as shown specifically in FIG. 1C, edge 138b of base 100. Shelf 620 may be configured to have a first portion 620a that extends in a plane parallel to a plate 410 and covers a portion of a bottom surface of base 100; a second portion 620b may be configured to extend in a direction approximately perpendicular to plate 410 and cover the proximal end or edge of base 100; and a third portion 620c (not shown) may be configured to extend in a plane that is parallel to plate 410 and cover a portion of a top surface of base 100. The first and third portions are vertically offset by the second portion. In embodiments, shelf 620 may have a height that is substantially the same as the thickness of base 100, such that the inner surfaces of shelf 620 are configured to be positioned adjacent to surfaces of base 100. Alternatively, shelf 620 may have a height that is larger than a thickness of base 100 to distance portion 620a or plate 410 from base 100.

In FIG. 1, shelf 620 is configured to be positioned or slide under at least a portion of the base 100, contacting edge 138b. One skilled in the ordinary art may appreciate shelf 620 may be configured to attach to base 100 in various ways based off the shape of plate 410 and shape of base 100. In FIG. 1, Shelf 620 may be positioned on any portion of the plate, including plate side 410e and/or side 410f and be configured to contact or cover base edge 138a and/or 138c, respectively. Shelf 620 may also be positioned on the bottom surface 410d, as shown, or on the top surface 410c. One skilled in the art will appreciate that any number of shelves may be positioned on the plate 410 and that where base 100 and plate 410 have alternative shapes, one or more shelves may be places along the surfaces, edges or ends of base 100 and plate 410 to achieve the desired coupling.

Figure 2A:
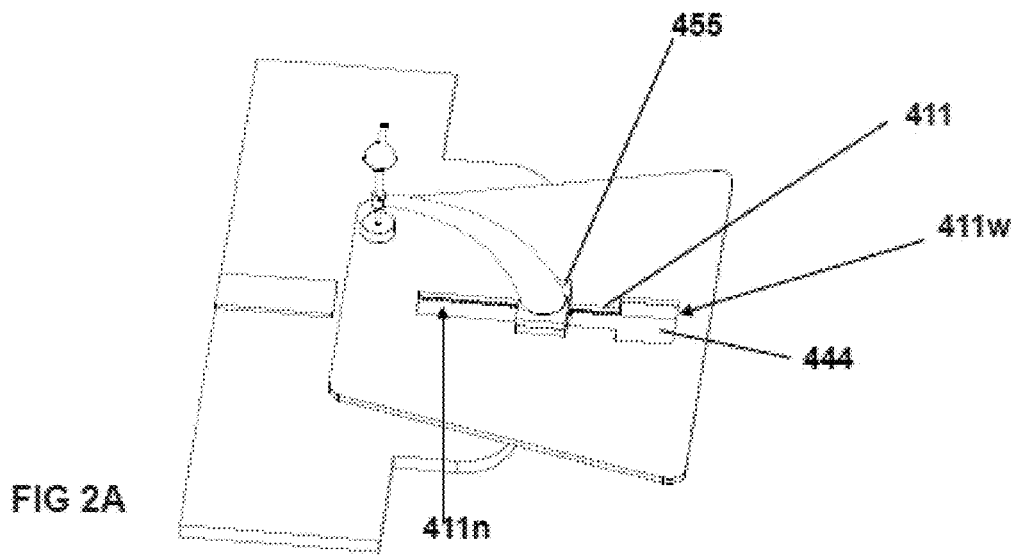
FIGS. 2A-2I show embodiments of a holder wherein a plate includes a recessed longitudinal translator.
Figure 2B:
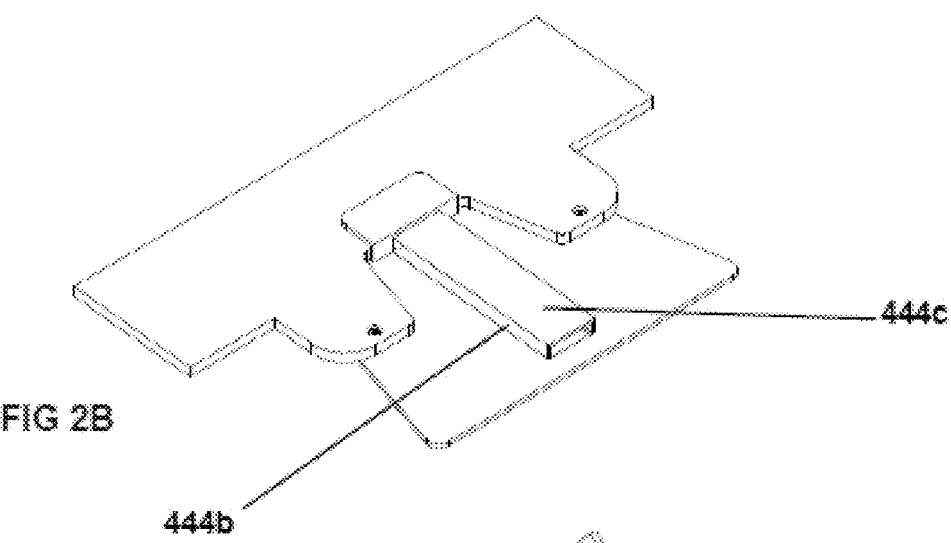

Shelf 620 may be coupled or secured to base 100 by bolts 211 (as shown in FIG. 1C) or shelf 620 may slide over base 100 to be coupled with base 100 without bolts 211 as shown in FIG. 2B. Alternatively, straps, bridges, clamps, or any other coupling mechanism may be employed to fasten shelf 620 to plate 100. Shelf 620 may be movable or fixed in position.

In embodiments, responsive to a patient applying downward force to plate 410, shelf 620 may be configured to allow the plate 410 to remain in a fixed position and provide additional support to couple plate 410. Shelf 620 may be configured to receive pressure from a patient sitting on plate 410, and distribute the pressure to the base 100.

FIG. 1D shows a side view of holder 400 in greater detail uncoupled from medical device 500. Plate 410 includes a longitudinal translator 450 designed to enable translation of stem 420 between plate's first end 410a and second end 410b. Longitudinal translator 450 consists of a motion system, comprised of a set of rails (hereinafter "rail 454") and carriage 455. In FIG. 1D, carriage 455 is capable of moving, sliding or translating along rail 454 between plate's first end 410a and second end 410b.

Carriage 455 may be coupled, attached or integral with stem 420 to enable longitudinal movement of stem 420 and attached device 500. Responsive to a practitioner applying forward or backward force on the stem 420, the longitudinal translator 450 would slide forward and back accordingly. The longitudinal translator 450 allows a physician to adjust the distance between the device 500 and the patient (or in this embodiment, the manipulator) and the vaginal intoritus for precise device placement.

FIG. 1D shows a particular embodiment of a longitudinal translator 450 configured as a linear motion system. However, any motion system, track or translation system may be substituted and suffice as longitudinal translator 450 in this and other embodiments throughout this specification. For example, carriage 455 may include ball, ball bearings, wheels, casters, grooves, or any feature to support motion. Rail 454 may be comprised of rails, channel, guiderails, groves, slides, gully, channels, tracks. In addition, bolts, screw, locks, fasteners, clips, clamps, or any other breaking feature configured to apply friction (hereinafter "brake 458") may be integrated with longitudinal translator 450 to enable braking or locking of the longitudinal translator 450. Although linear systems are preferred for easy of assembly, one skilled in the art may appreciate that the longitudinal translation system need not be perfectly linear, but for example may also be curved or non-linear. FIG. 18 to FIG. 21 describe alternative motion system embodiments in further detail.

Plate 410 includes a receptacle, cutout, aperture, recess, groove, or opening (hereinafter "cutout 411") configured for creating access to longitudinal translator 450 and its components. However, in embodiments, longitudinal translator 450 or its components may be positioned within, below, or on top of plate 410, which would not necessarily require a cutout 411. Longitudinal translator 450 or its constituent components (rail 454 or carriage 455) may also be positioned on a lower or upper surface of Plate 410. Additionally, cavity 138 may be utilized to house longitudinal translator 450, thereby allowing the carriage 455 to move within cavity 138.

Longitudinal translator 450 may be positioned between the plate's first end 410a and the second end 410b in a straight, segmented, or curved line. In embodiments wherein base 100 contains a cavity 138, longitudinal translator 450 may transverse across cavity 138, as shown in FIG. 1C.

Stem 420 is comprised of a first end 420a coupled to or integral with longitudinal translator 450 and a second end 420b configured to couple to a vertical translator 490, rotational translator 470, and/or device coupler 430. Based on the positioning of longitudinal translator 450, stem's second end 420b may extend past or distal to plate's second end 410b. The longitudinal translator 450 may directly couple to stem 420 via bolts 211, glue, welding, or any other coupling mechanism, or alternatively be integral with stem 420. FIG. 1D shows the stem arching, bent, or curving concavely where at least a portion of stem 420 is positioned at an angle relative to the plate (between 0 and 90 degrees), wherein the stem 420 is curved towards base 100. This arched concave stem shape is desirable to prevent the patient's posterior from sliding into the stem 420 in a traumatic or invasive orientation. This arched concave stem shape also enables easy and ergonomic gripping by a practitioner, especially during manual translation of carriage 455 between the first end 410 and second end 410b. For example, if positioned is moved from a trendelenburg to a reverse trendelenburg position, the patient's pelvis is likely to slide down and may slide into stem 420. Additionally, the curvature of the stem 420 may be based on the curvature of a patient to enable device 500 to atraumatically be positioned into a patient's body cavity.

In other embodiments, stem 420 may be any desired configurations of curves, angles, lines, shape and/or size. For example, the stem 420 may have no curvature or may curve convexly. Stem 420 and may be angled perpendicular, obtusely or acutely with respect to plate 410. A portion of stem 420 may be positioned at an angle relative to the plate (between 0 and 180 degrees). Stem 420 may a right angle bend or a joint in between the first and second end that allows pivoting or rotation.

Stem 420 may be rigid as shown, or may be flexible or adjustable. For example, stem 420 may be flexible or adjustable with respect to it's length, height, or position. For example, stem 420 may have a gooseneck 405, so it is malleable into any desired curved or straight orientation as the physician may prefer, as shown in FIG. 17.

As shown in FIGS. 1C & 1D, the position of the device 500 along the vertical Y axis may be adjusted via a vertical translator 490, which is configured to couple to stem 420. A medical practitioner may apply a force to the vertical translator 490 to increase or decrease the vertical offset 410y of device 500 from base 100, thereby accommodating variations in patient size. For example, when device 500 is a uterine manipulator, distance 410y may be adjusted to accommodate differences in distance between the vaginal introitus and base 100. In embodiments, vertical translator 490 may be configured to adjust the vertical offset of device 500 in a direction that is perpendicular to base 100 or in a direction that is set at an angle with respect to base 100.

In FIG. 1, vertical translator 490 is comprised of a large tube, stick, rail or shaft (herein "sliding tube 491") configured with threads and a base portion 492, and a coupling portion 420c configured as a hole or aperture ("aperture 420h") stem 420b's second end to receive, attach or couple sliding tube 491 to stem 420. When base portion 492 is rotated, sliding tube 491 vertically translates through aperture 420h, which may also has receiving threads on its inner surface.

In embodiments, base portion 492 may be any device configured to receive force to vertically move sliding tube 491. For example, base portion 492 may be configured to receive force in a direction that corresponds to vertical movement of sliding tube 491, or may receive force in a direction that is perpendicular to the vertical movement of sliding tube 491.

In embodiments, coupling portion 420c may be a hole or aperture ("aperture 420h), as shown in FIG. 1, or alternatively any other coupling means, including a clamps, cam-locks, carriages, bolts, pins, pull pins, fasteners, screw, or adhesives, (hereinafter "fastener 420f"), or some combination of both an aperture 420h and fastener 420f. For example, FIG. 10, shows an embodiment where coupling portion 420c includes an aperture 420h to fit or receive sliding tube 491 and a fastener 420f in the form of a side-pin 491p to lock sliding tube 491 into a fixed position. Responsive to applying force to base portion 492 to move sliding tube 491 to a desired height, coupling portion 420c may be configured to selectively lock sliding tube 491 in place via the side-pin. When it is desired to move sliding tube 491, the side-pin 491p may be pulled to unlock shaft for vertical translation.

In embodiments, vertical translator 490 may comprise a motion system modeled off of or comprised of a linear motion system. For example, coupling portion 420c may be a carriage and sliding tube 491 may be a rail. The carriage and rail embodiments may be similar to those described for the longitudinal translator 450 in this specification. Alternatively, the coupling portion 420c and sliding tube 491 may together comprise a non-linear motion system that achieves vertical translation.

Holder 400 may also include a rotational translator 470 to allow rotational motion of device 500 when attached to holder 400. Rotational translator 470 allows device 500 to be angularly rotated about a central point in multiple orthogonal directions. Rotational translator 470 may be integral with vertical translator 490 or be coupled to the vertical translator 490 via glue, welding, screws, pivot joints, hinge joints, ball and socket joints, or any other coupling or fastening mechanism.

FIG. 1 illustrates an embodiment wherein rotational translator 470 is comprised of a spherical bearing or ball 464 and socket or cap 465 positioned on the ball's outer circumference, wherein the cap rotates freely around ball 464. In this ball-and-socket embodiment, cap 465 is configured for coupling to device 500 to enable free rotation of the device while ball 464 is coupled or affixed to the vertical translator 490. However, in other embodiments, ball 464 may be configured for coupling to device 500, while cap 465 is fixed to the vertical translator, as shown in FIG. 14B.

Ball 464 may include a channel 464c (see FIGS. 13G and 13H) extending through the rotational ball 464, configured to receive and couple to the vertical translator 490 or one of its components. In this embodiment channel 464c contains threads to receive sliding tube 491. In other embodiments, vertical translator may be integral with the ball, or be separate and affixed by glue or another fixing mechanism.

In embodiments where ball 464 is configured for coupling to device 500, ball 464 may have a channel for receiving a component of device 500, or may have no channel but a protrusion for coupling to device 500. The protrusion may be threaded or not-threaded. Alternatively, the protrusion may have a camlock, clip or device coupler 430 to couple to device 500, as shown in FIG. 14B.

FIGS. 14-16 show different embodiments of rotational translators in more detail.

Holder 400 may include device coupler 430 configured to fasten, couple or secure holder 400 to device 500. In the embodiment shown in FIG. 1, device coupler 430 is a screw projection with threads configured to screw into a receiving body 501 with a receiving threaded portion of device 500. In other embodiments, device coupler 430 may be a simple projection without threads. FIG. 1 shows the device coupler on cap 465, however in other embodiments, it may be positioned on ball 464 (e.g., FIG. 14B) or any other portion of rotational translator 470.

As shown in FIG. 10, device coupler 430 may include a clasp, clip, or clamp (hereinafter "clamp 431") to fasten, mechanically join or affix holder 400 to device 500 or its component, such as a tube.

Thus, a device 500 coupled device coupler 430 (and holder 400 by extension) to may be configured to move and rotate in a plurality of different directions and angles. Device coupler 430 may have 360 degrees of rotational freedom or less. In the embodiments shown, device coupler 430 is coupled to a rotational translator 470, vertical translator 490, in addition to being coupled to the stem and longitudinal translator 450, which enables the range of motion along the X and Y axis in addition to the rotational freedom. In embodiments, such as FIG. 6, device coupler 430 is coupled to a lateral translator 480 and may move along the Z axis, thereby creating an additional plane of movement for device coupler 430 and coupled device 500 and achieving 6 degrees of freedom. Embodiments throughout this specification with 5 degrees of freedom may be modified to achieve 6 degrees of freedom, or vice-versa by modifying translator components.

Cap 465 may assist in controlling the rotation of device coupler 430. In embodiments, device coupler 430 may be directionally positioned and rotationally positioned at any desired offset distance from plate 410 and/or angle through adjustments of the sliding tube 491 and/or rotational ball 464.

Figure 2C:
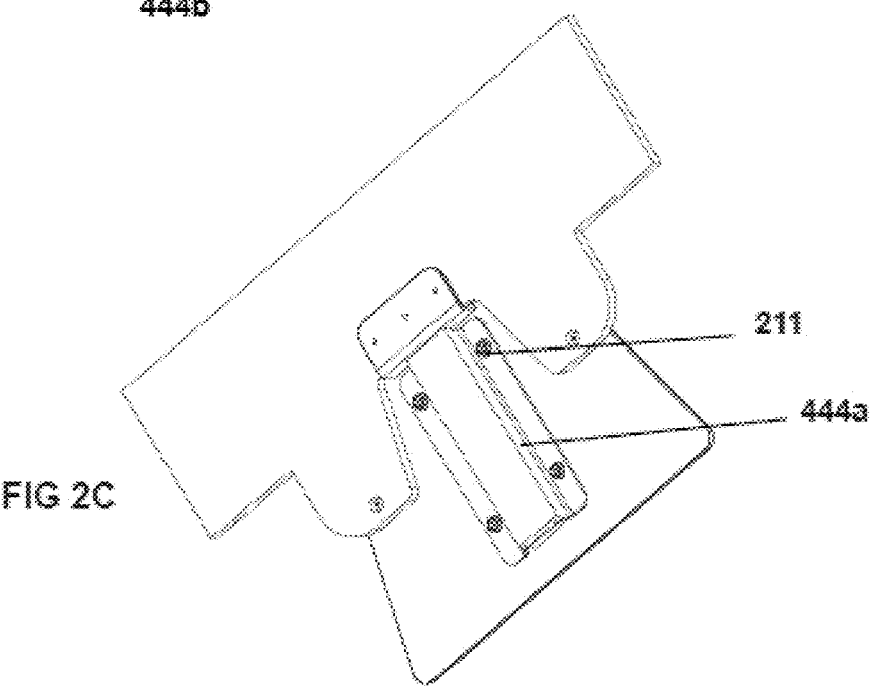
Figure 2D:
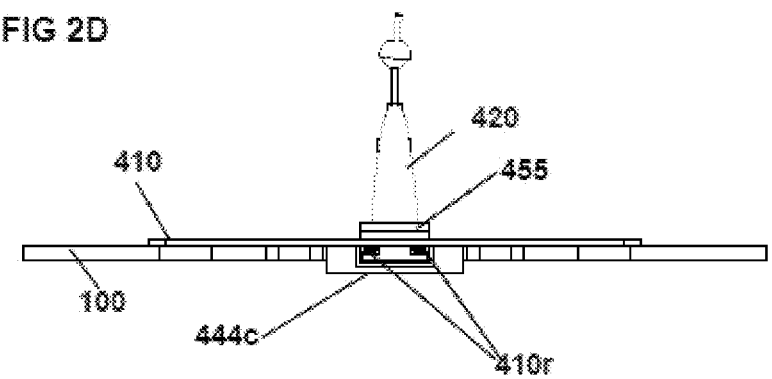

FIGS. 2A-2I shows an embodiment of holder 400 wherein plate 410 includes a recessed longitudinal translator 450. FIG. 2A offers a top angled view, showing longitudinal translator 450 positioned within cutout 411, comprised of a carriage 455 sliding longitudinally along track 444. FIGS. 2B and 2C offer bottom angled views of two embodiments wherein track 444 is integral with plate 410 and/or shelf 620 (FIG. 2A), or secured via bolts 211 to plate 410 (FIG. 2B). Track 444 has sidewalls 444a and 444b and a bottom surface 444c. Track 444 may extend below base 100 or plate 410. However, in other embodiments, track 444 may be configured to be positioned on top of or coplanar with base 400 or plate 410. FIG. 2D is a side view from the proximal end of holder 400 and track 444.

Figure 2E:
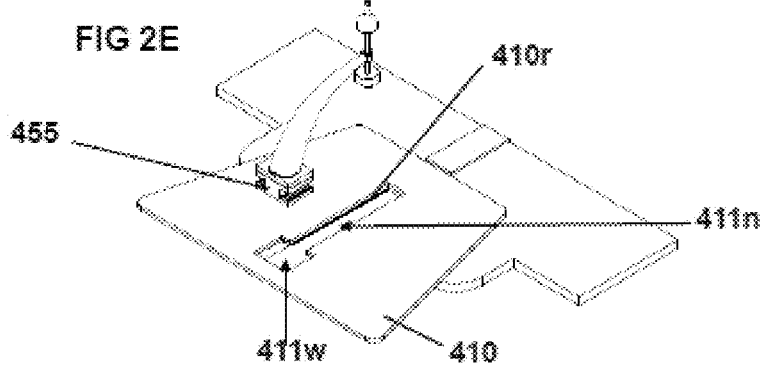
Figure 2F:
Figure 2G:
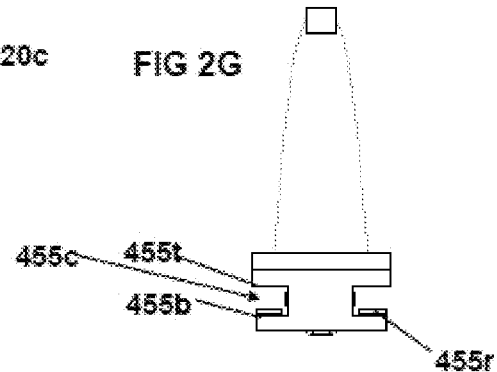

FIG. 2E shows how in an embodiment, cutout 411 may be configured to have a narrow portion 411n and a wide portion 411w. Narrow portion 411n enables secure and stable translation of carriage 455. Due to the decreased width of narrow portion 411n, carriage 455 may not be removed from track 444 while positioned within narrow portion 411n. In other words, if carriage 455 is raised while positioned within narrow portion 411, the sidewalls of narrow portion 411n may restrict the vertical movement of carriage 455.

Wide portion 411w enables retrieval and insertion of carriage 455 into track 444. Due to the increased width of wide portion 411w, longitudinal translator 450 may be vertically removed and decoupled from plate 410 when positioned within wide portion 411w. Wide portion 411w is positioned at the proximal portion of plate 410 to facilitate easy of retrieval and insertion at the maximum distance from the patient, however it may be positioned at any point along cutout 411. Carriage 455 is positioned above plate 410 to illustrate its position before insertion or after removal. In other embodiments, carriage 455 may not be removable.

One skilled in the ordinary art may appreciate that cutout 411 may have different shapes, which may or not correspond to a shape of carriage 455. Cutout 411 may also be uniform in dimension without wider or narrow portions. The opening may extend all the way to plate's proximal and/or distal ends 410a and 410b, so the longitudinal translator 450 in inserted from the plate end 410a or 410b.

FIGS. 2F-2I show alternative perspectives of an embodiment of carriage 455 wherein it has an hourglass shape wherein the middle diameter is less than the top and bottom diameters. Alternatively stated, carriage 455 may have one or more cavities 455c which house or fit plate 410 and the enable the carriage 455 to slide along the surfaces of plate 410. For example, cavity 455c may have an upper surface 455t and lower surface 455b which respectively slide against plate's top surface 410c and bottom surface 410d.

One skilled in the ordinary art may appreciate that longitudinal translator 450 and plate 410 may integrate components of any motion system to enable smooth translation. For example, carriage 455 may be any linear motion carriage and track 444 may incorporate a linear motion rail to facilitate motion.

Holder 400 may include various locking or brake mechanisms to lock the longitudinal translator 450 into place without slippage. FIG. 2 illustrates an embodiment wherein carriage 455 includes a corrugated surface 455r on the lower surface 455b (FIG. 2G) and plate 410 has a similar corrugated surface 410r on the bottom surface 410c of the plate (FIG. 2E), such that when the surfaces 455r and 410r lock, carriage 455 is prevented from moving. Corrugated surface may include C, V, C, T, W, S, L, rectangular, circular, or polygonal shaped corrugations. The corrugated surface may include angled corrugations (for example angled Z corrugations) configured to enable sliding in one direction but restrict movement in the opposite direction. Corrugated surfaces may be placed on any surface of the carriage 455, track 444, and/or plate 410. For example, corrugated surfaces may be on the plate's top surface 410b and carriage's upper surface 455t.

Figure 2H:
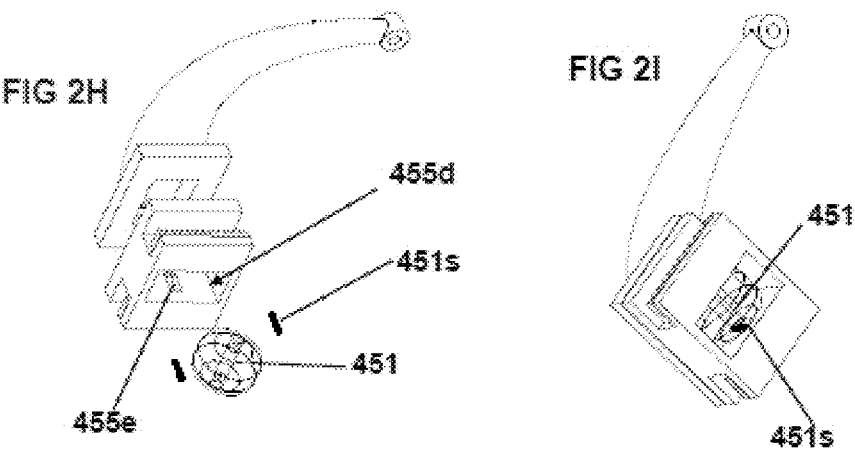
Figure 2I:
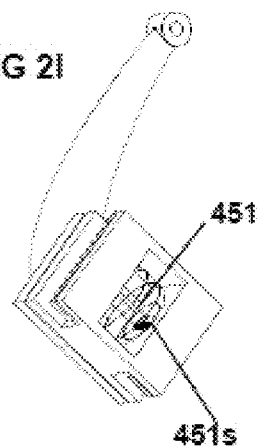

As shown in FIGS. 2H and 2I, carriage 455 may include a cavity 455d to house a ball or wheel 451 for smooth translation. Wheel 451 may be spring-loaded via springs 451s to enable locking and unlocking with corrugated surfaces. In the embodiment shown, when a practitioner applies downward force to the stem 420, spring 451s compresses, distancing corrugated surfaces 455r and 410r from one another, thereby unlocking the two corrugated surfaces, and enabling the practitioner to move carriage 455 forward or back. Releasing the stem 420 causes the spring to expand and lock the two surfaces 455r and 410r together.

Figure 3A:
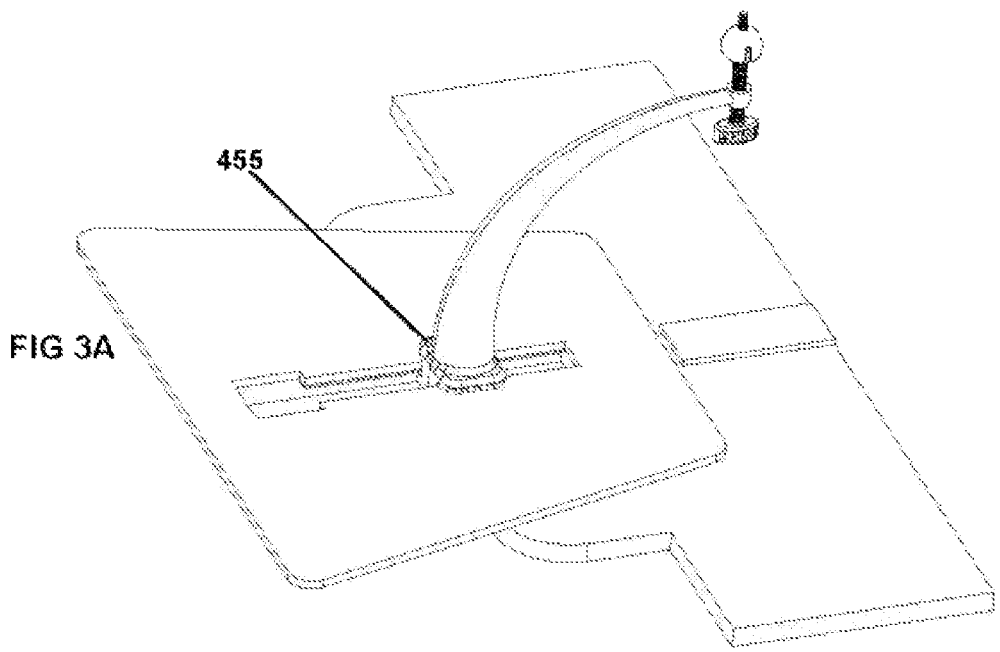
FIG. 3A-3E depicts embodiments of a carriage.
Figure 3B:
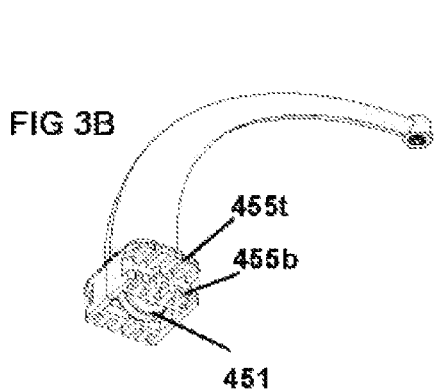
Figure 3C:
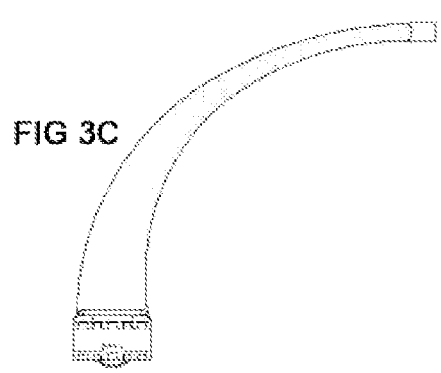
Figure 3D:
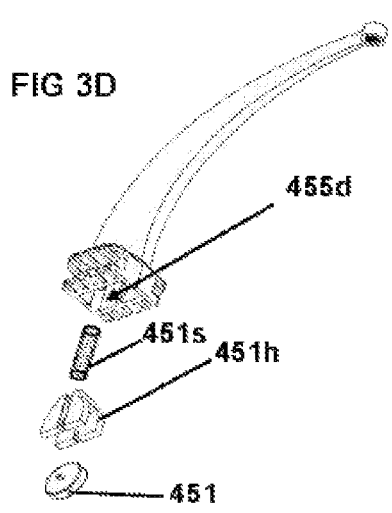
Figure 3E:
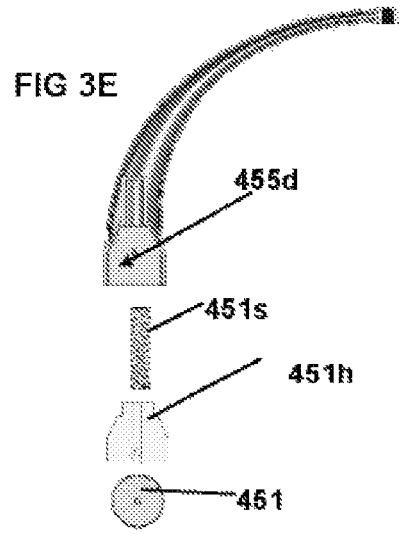

FIG. 3A-E depicts embodiments of carriage 455. FIG. 3A depicts an embodiment of carriage 455 positioned within plate 410. FIG. 3B illustrates a perspective view of the embodiment, showing ridges on upper surface 455t and lower surface 455b of carriage 455. FIG. 3C illustrates a side-view of the embodiment. FIG. 3D shows an exploded perspective view of a spring-loaded wheel, wherein housing 451h couples spring 451s to wheel 451 within cavity 455d. FIG. 3E shows a cross-sectional view.

Figure 4A:
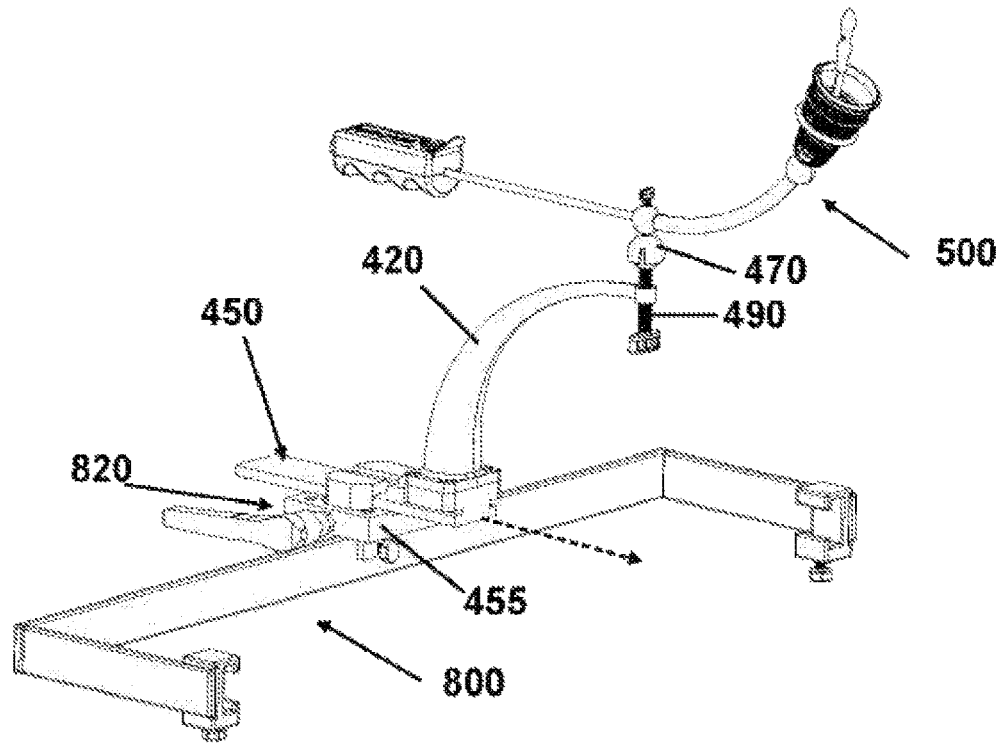
Figure 4B:
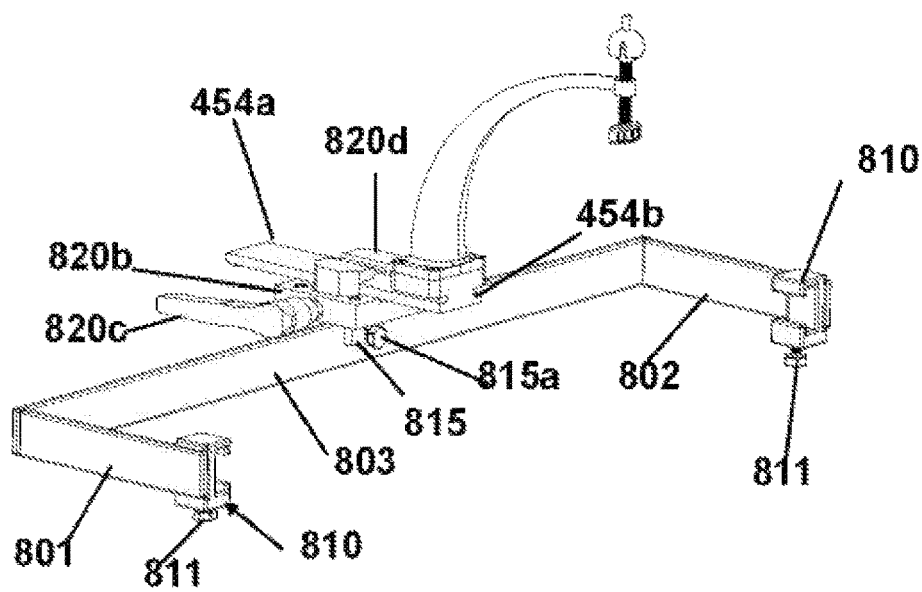
Figure 6A:
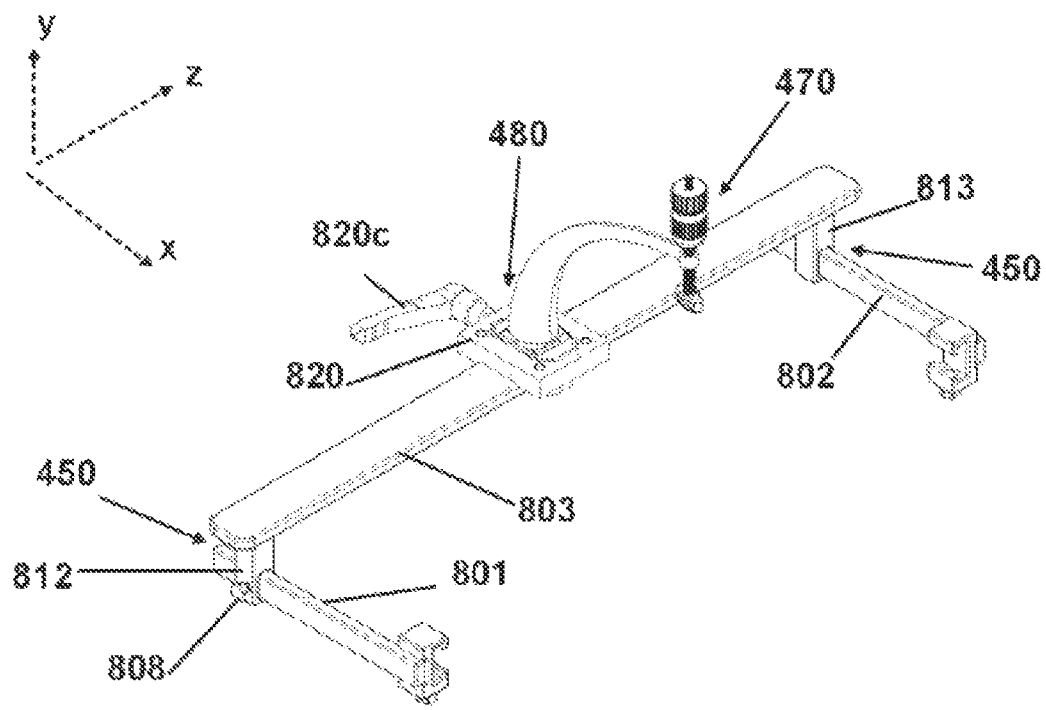
FIGS. 6A-6E illustrate a perspective, side, bottom, top and front views respectively of a similar embodiment wherein the longitudinal translator is comprised of an elongated body with constituent carriages that slide on arms, or a portion thereof, which serve as rails.
Figure 6B:
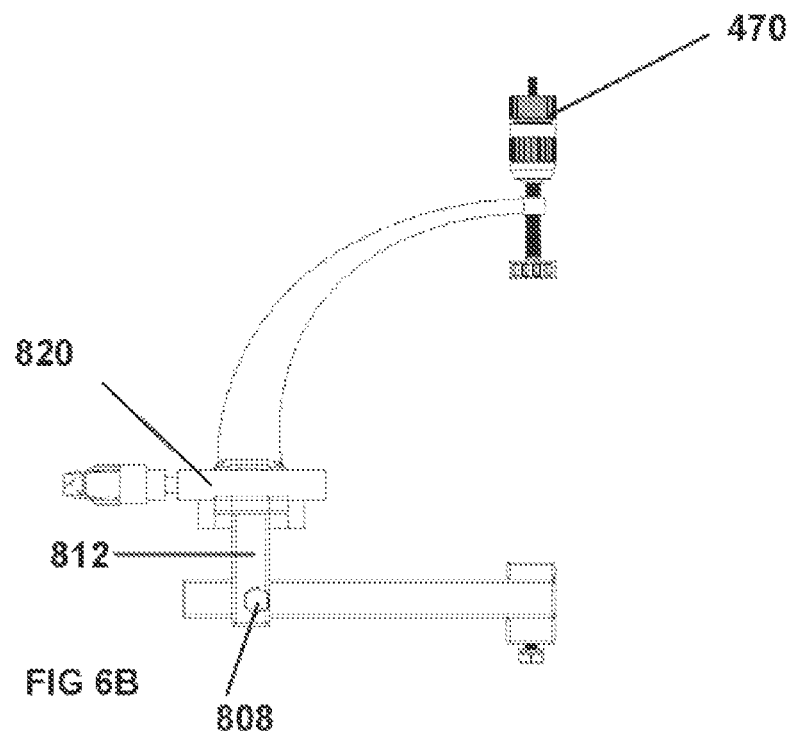
Figure 6C:
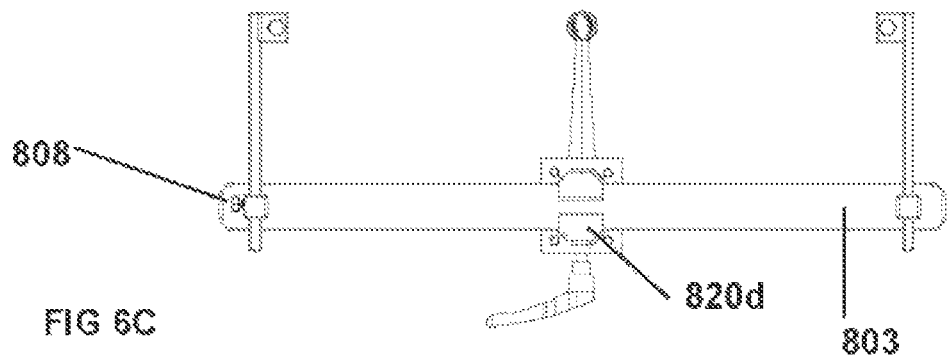
Figure 6D:
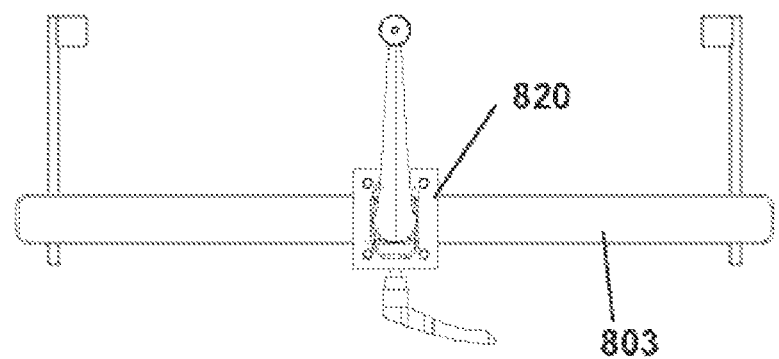
Figure 6E:
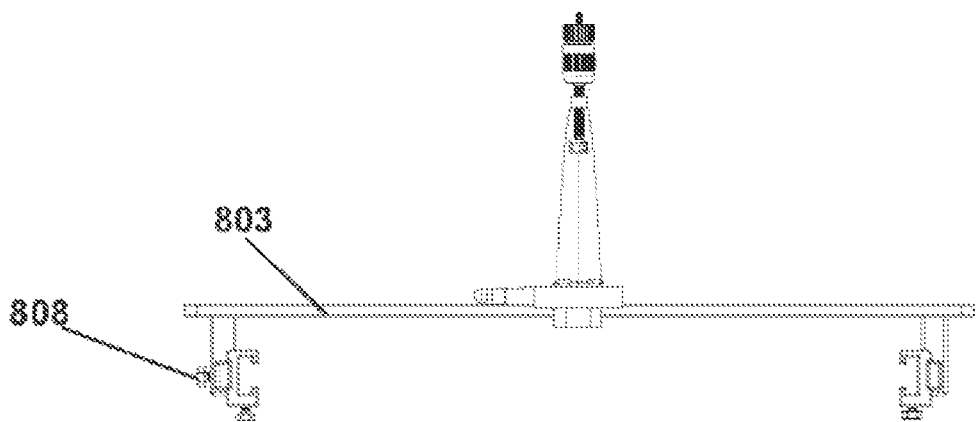

FIGS. 4A-4E illustrate an alternative embodiment, wherein holder 400 is configured to couple to device 500 and the side-rails or extended protrusions of an operating table. FIG. 4A shows a perspective view of an embodiment of holder 400 coupled to a medical device 500, whereas FIG. 4B shows the same view of holder 400 without the medical device 500. FIG. 4C is an additional perspective view of the embodiment, FIG. 4D a top view, and FIG. 4E a bottom view.

Like embodiments described above, holder 400 may include but is not limited to a stem 420, rotational translator 470, vertical translator 490, lateral translator 480, device coupler 430, and may incorporate features or variations previously or subsequently described in this specification.

FIG. 4's embodiment may also include a side-rail attachment 800 (hereinafter "attachment 800") to affix or attach holder 400 to the operating table in lieu of plate 410. FIG. 10B illustrates an embodiment of an attachment 800 coupled to side-rails 101 and 102 of base 100.

Figure 27:
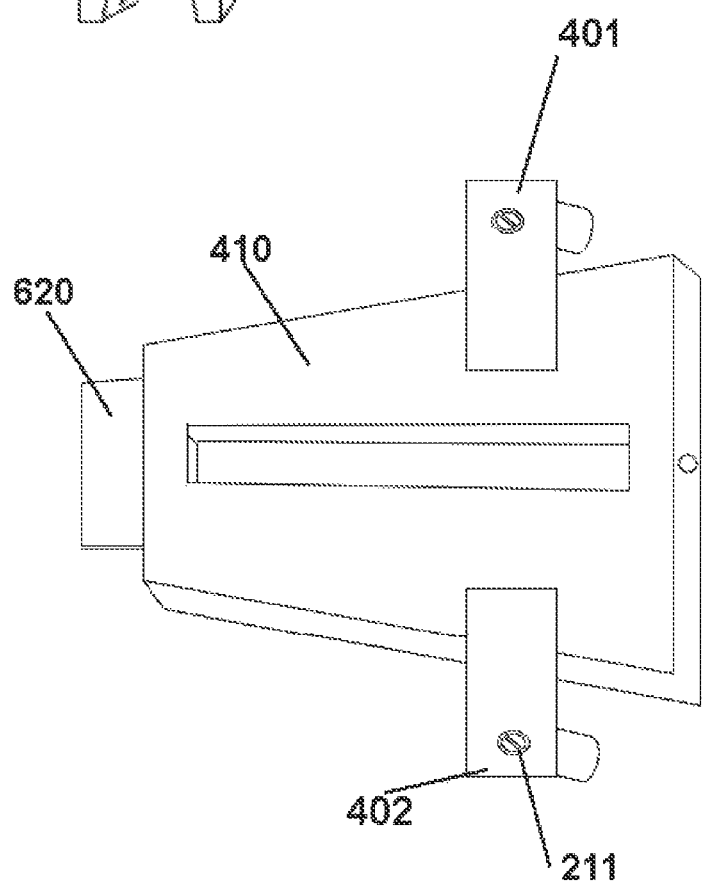
FIG. 27 illustrates an embodiment wherein arm attachments and a plate are combined to form a hybrid attachment to the base of an operating table.

One skilled in the ordinary art may appreciate that plate 410 and attachment 800 are not mutually exclusive and may both be employed or integrated in part or whole into an embodiment of holder 400. For example, FIG. 27 shows an embodiment wherein plate 410 has two arm attachments 401 and 402 which attach or couple plate 410 to base 100 by bolts 211.

FIG. 4B illustrates that attachment 800 may be comprised of an elongated body 803, a first arm 801 and second arm 802, which respectively attach to side-rails of an operating table. Experiments have shown the distance between first arm 801 and second arm 802 for operating tables in North America is between 20 and 22 inches. One skilled in the art will appreciate that rail attachment need not be square or rectangular with perpendicular arms, but may also be rounded, oval or any polygonal shape with angled, curved or straight arms. One skilled in the art will appreciate that rail attachment may attach to any rail like portion or protrusions of an operating table.

FIG. 4B shows arms 801 and 802 may include or be coupled to a respective fastener, clip, collar, coupling mechanism, or clamp 810 (hereinafter "clamp 810"). Clamps 810 may include respective knobs, bolts, clamps or screws 811 to secure or couple clamps 810 and by extension arms 801 and 802 to side-rails. Screws 811 may be positioned on bottom, top or the side of clamp 810, and may be ergonomically shaped to facilitate attachment and removal after procedures. Arms 801 and 802 may be attached to side-rails by other means including Velcro, adhesives, etc. Alternatively, attachment 800 may be permanently attached to side-rails or may be an extension of side-rails as one integral unit.

In the embodiments shown, clamps 810 is on the inner surface of arms 801 and 802. However, clamp 810 may also be positioned on the bottom, top or exterior surface of arms to enable attachment to any protrusions, extensions, rails or side-rails of an operating table. In some embodiments, clamp 810 may be comprised of a weight or fitting onto the end of a surgical platform or operating table.

FIG. 4B shows that longitudinal translator 450 is comprised of a rail 454 which translates or slides longitudinally through a fixed clamp or carriage 455. This embodiment is a "reverse linear motion system", wherein the linear carriage is fixed, and the linear motion rail translates, as opposed to a "normal linear system" wherein the linear carriage translates along a fixed linear motion rail. This reverse configuration enables a medical practitioner to slide the rail away from the operating table if needed.

Rail 454 has a first end 454a and second end 454b configured for translation through carriage 455. Rail 454 may be rectangular, oval, or any elongated shape and may have one or more grooves or an hourglass shape to facilitate smooth translation. Stem 420 may couple or integrate with Rail 454 at any portion, including the second end 454b as shown. FIG. 4 shows an embodiment where carriage 455 may be configured as a clamp 820 with a base 820b, a hand actuated lever or handle 820c, and teeth 820d which the rail 454 slides through. Responsive to twisting or turning handle 820c, clamp opens to allow translation of the rail 454, or if turned in reverse, closes to fix the position of the rail 454. Teeth 820d may have sufficient height to limit, prevent, reduce, etc. the translation or movement of the rail 454 off the carriage. In embodiments, carriage 455 is not configured as a clamp but as a simple carriage without a braking or locking system.

FIGS. 4C and 4E shows carriage 455 may couple to attachment 800 via a fastener, attachment clamp or coupler 815 (hereinafter "coupler 815"). In this embodiment, coupler 815 is comprised of two parallel plates, wherein the plates are positioned perpendicular to carriage 455 or clamp 820 and rail 454. The parallel plate may be configured to sandwich or slide into attachment 800, or elongated body 803 as shown. Coupler 815 may be in a single fixed position or may slide or move along elongated body 803. Coupler 815 may include a bolt or lock screw 815a for coupling carriage 455 into a fixed position. Alternatively, coupler 815 may be integral with attachment 800 in a fixed position.

FIG. 4D shows a top view of the embodiment, illustrating how rail 454 is positioned within teeth 820d of clamp 820. Teeth 820d may be opened or closed via handle 820c thereby allowing or restricting movement of rail 454.

FIG. 5A-5C illustrates a perspective, top and bottom views respectively of a similar embodiment as FIG. 4A. In this embodiment, however, holder 400 is comprised of a standard or "normal linear motion system" wherein rail 454 is fixed onto attachment 800 via coupler 815 and carriage 455 translates along rail 454 longitudinally. Coupler 815 may include elements described elsewhere in this specification. For the sake of brevity a further description of these elements is omitted.

This embodiment also includes a backstop 454s to prevent carriage 455 from sliding off rail's first end 454a. Backstop 454s may also be positioned at second end 454b to prevent carriage 455 from sliding off the second end. Backstop 454s may be incorporated in any linear motion system (reverse or normal), or any of the longitudinal or vertical translators mentioned throughout this specification. This embodiment also includes an alternative rotational translator component 470 shown in further detail in FIGS. 15A-15F.

FIGS. 6A-6E illustrate a perspective, side, bottom, top and front views respectively of a similar embodiment wherein the longitudinal translator 450 is comprised of the elongated body 803 with constituent carriages ("carriage 812" and "carriage 813") that respectively slide on arms 801 and 802, or a portion thereof, which serve as rails. Together, the elongated body 803, carriages 812 and 813, and arms 801 and 802 comprise a linear motion system. A linear motion brake, side clamp, lock or screw (hereinafter "brake 858") may be configured on one or both carriages 812 and 813 to enable locking the elongated body 803 into a fixed position and achieving a fixed length of longitudinal translation along the x-axis.

Carriage 455 may be fixed in position on elongated body 803 or, as shown in FIG. 6, may be configured as a slidable carriage or clamp 820 which may slide along elongated body 803 on the lateral or z axis, perpendicular to the longitudinal translation on the x axis or at an offset from the x axis, thereby constituting a lateral translator 480. Handle 820c may be actuated to open or close teeth 820d and enable lateral motion or braking respectively of carriage 455 along elongated body 803. One skilled in the art can appreciate that carriage 455 may be any carriage described throughout this specification, and may include a brake, for example with braking features such as a clamp, lock, screw or camlock. One skilled in the art can appreciate that this embodiment may be integrated in part or whole with plate 410. This embodiment also includes an alternative rotational translator component 470 shown in further detail in FIG. 16.

Figure 7A:
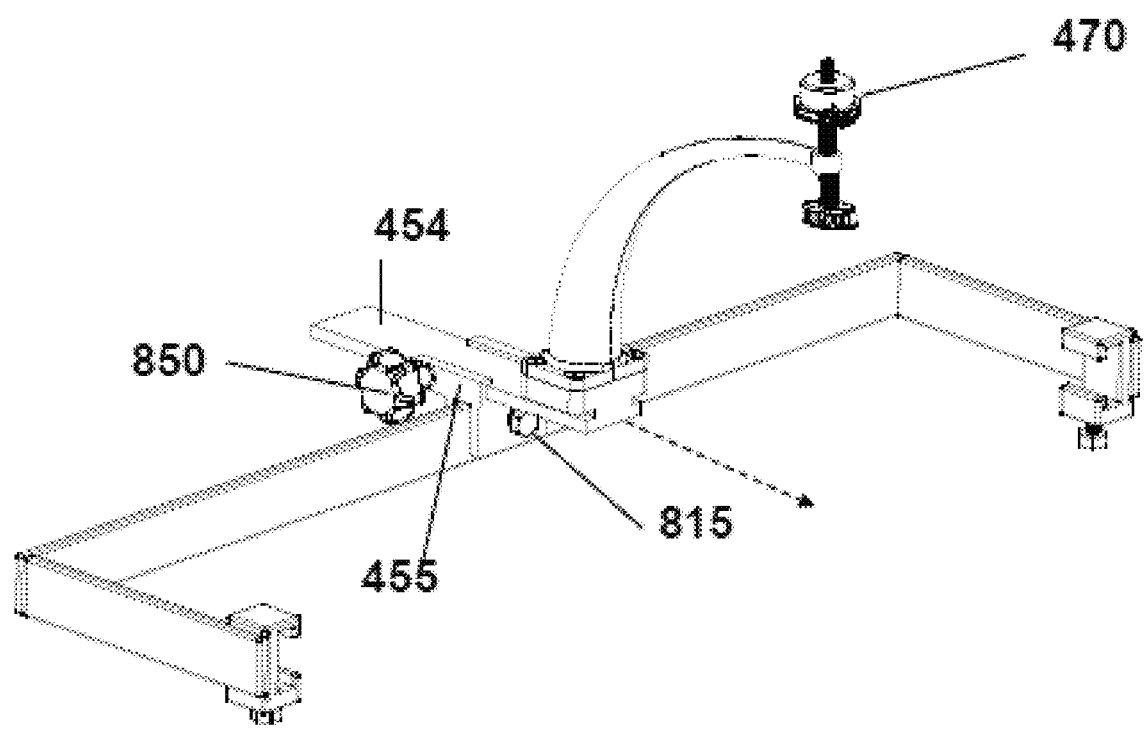
FIGS. 7A and 7B illustrate an embodiment similar to FIG. 4, wherein a reverse linear motion system is configured to translate through a fixed carriage.
Figure 7B:
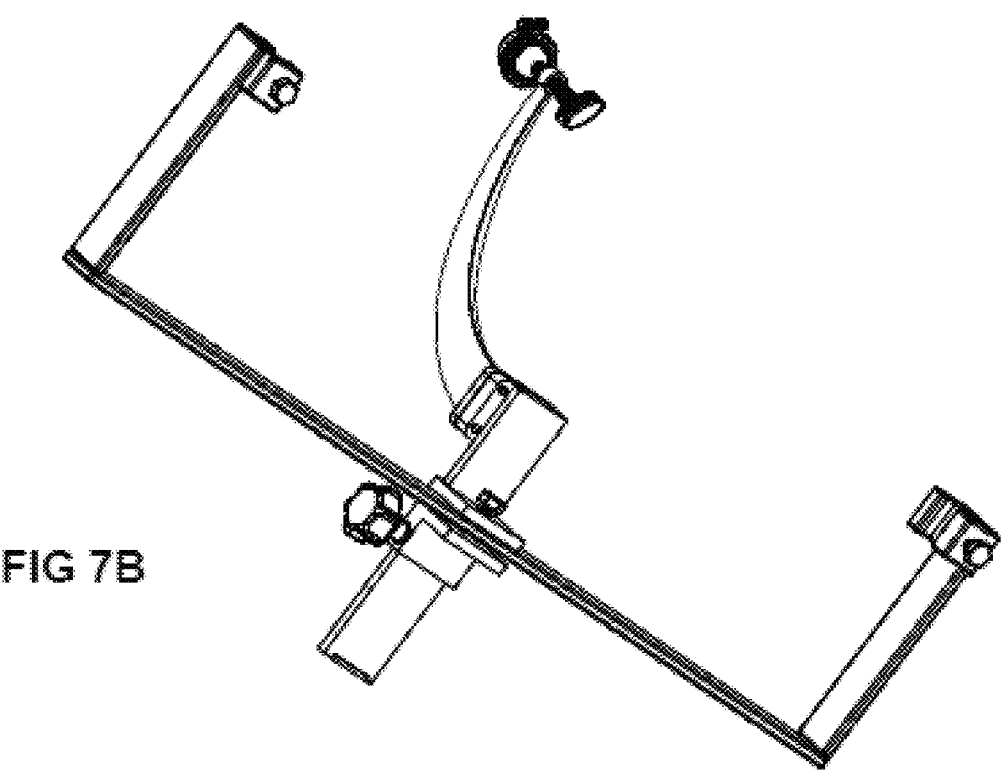

FIGS. 7A and 7B illustrates an embodiment similar to FIG. 4, a "reverse linear motion system" wherein rail 454 is configured to translate through a fixed carriage 455. In this embodiment, carriage 455 is configured with a side-screw 850. Side-screw 850 may be configured for locking rail 454 into position, rather than a hand actuated lever or handle. Alternatively, side-screw 850 may also be a rotating or rolling screw, which upon turning clockwise or counterclockwise translates rail 454 in a direction (e.g., forward or back). One skilled in the art may appreciate that a rolling screw may also be part of a "normal linear system" wherein the rail 454 is fixed and carriage 455 translates. In such an embodiment, when rolling screw is turned, carriage 455 translates along rail 454.

In addition, carriage 455 is integrated with coupler 815 as one unit, having a screw 815a to secure the position of carriage 455 along the elongated body 803. FIG. 7 also includes an alternative rotation translator shown in further detail in FIG. 15.

Figure 8A:
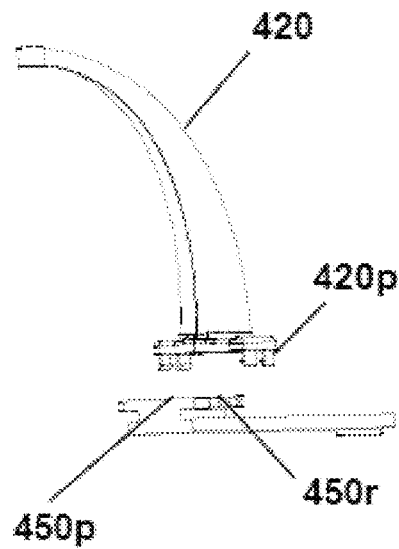
FIGS. 8A-B show perspective views of an embodiment of a detachable stem.
Figure 8B:
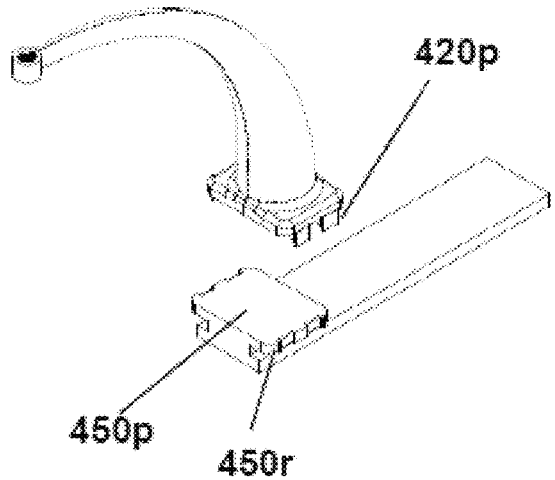

FIGS. 8A-B show perspective views of an embodiment of a detachable stem 420. In this embodiment, stem 420 may include male buttons, tabs, or protrusions 420p that snap into a female receiving portion 450r on platform 450p, which may be part of or coupled to rail 454 or carriage 455, depending on whether the longitudinal translator is a reverse or normal linear motion system.

Figures 9A, 9B:
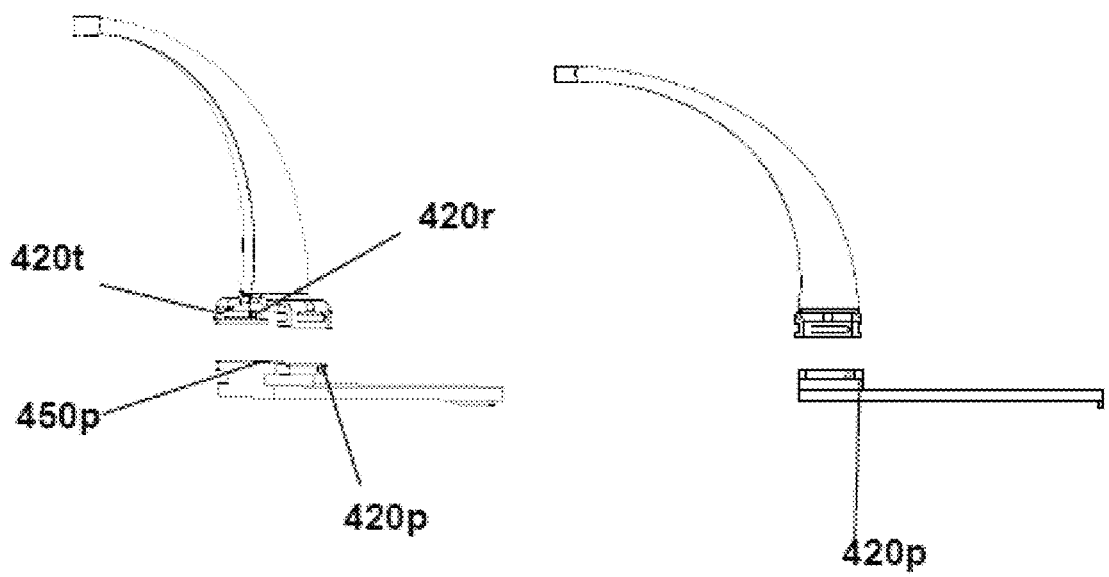
FIGS. 9A-B shows a side and perspective view of another detachable stem embodiment wherein a platform includes male protrusions which pressfit into a female receiving portion on the stem's first end.

FIGS. 9A-B shows a side and perspective view of another detachable stem embodiment wherein platform 450p includes male protrusions 420p which pressfit into a female receiving portion 450r on the stem's first end 420a. Stem 420 may also include an inner track 420t to slide in protrusion 455b. One skilled in the ordinary art can appreciate that male and female and male mating parts may be placed on either components (stem or longitudinal translator) to ensure coupling. As shown in previous embodiments, stem 420 may also be attached to carriage 455, which may also include similar platform, protrusions, track or receiving portions.

Figure 10A:
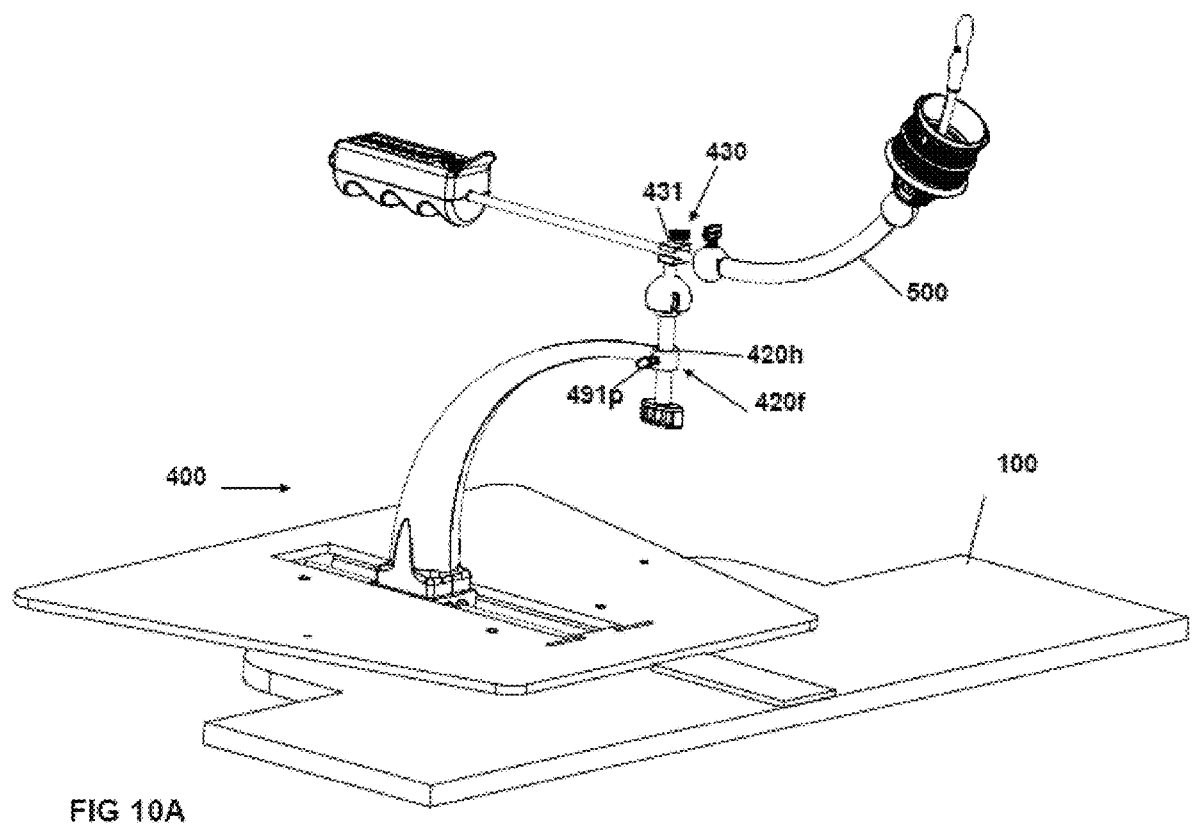
FIGS. 10A and 10B show perspective views of embodiments where a fastener in the form of a side-pin locks a sliding tube into a fixed position and where a clamp fastens the holder to a device.
Figure 10B:
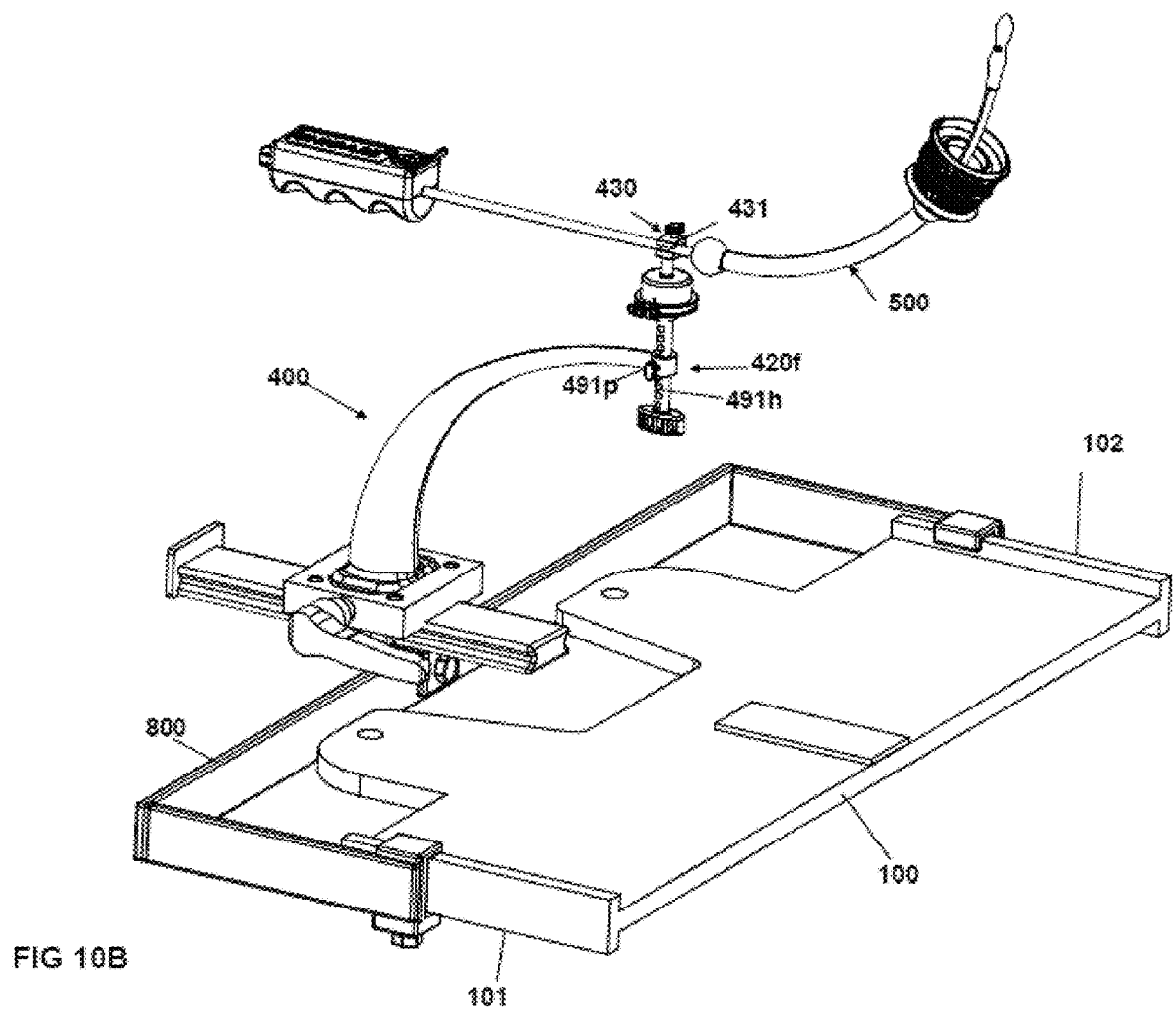

FIGS. 10A and 10B illustrate how elements described throughout this specification may be substituted by other like elements for new configurations or modifications. FIG. 10A shows an assembly of holder 400, device 500 and base 100 similar to FIG. 1A, and FIG. 10B shows an assembly of holder 400, device 500 and base 100 similar to FIG. 5A. However in both embodiments, coupling portion 420c includes an aperture 420h to fit or receive sliding tube 491 and a fastener 420f in the form of a side-pin 491p to lock sliding tube 491 into a fixed position. In addition, in the embodiment, device coupler 430 includes a clamp 431 to fasten, mechanically join or affix holder 400 to device 500 or its component, such as a tube. In FIG. 10B, sliding tube 491 additionally has holes 491h to receive side-pin 491p. FIG. 10B also illustrates attachment 800 configured to side-rails 101 and 102 of base 100. One may appreciate that the stem 420 in either of these embodiments with side-pin 491p and clamp 431 may be coupled to any linear translator in this specification.

Figure 11:
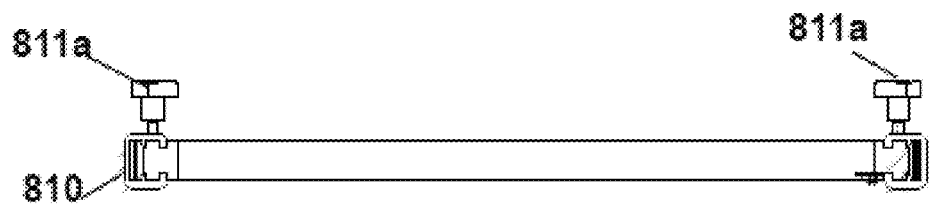
FIG. 11 shows an embodiment of an attachment where screw is configured with an ergonomic knob for twisting.

FIG. 11 shows an embodiment of attachment 800 where screw 811 is configured with an ergonomic knob 811a for twisting. Any screw or lock throughout this specification may have similar ergonomic features.

Figure 12A:
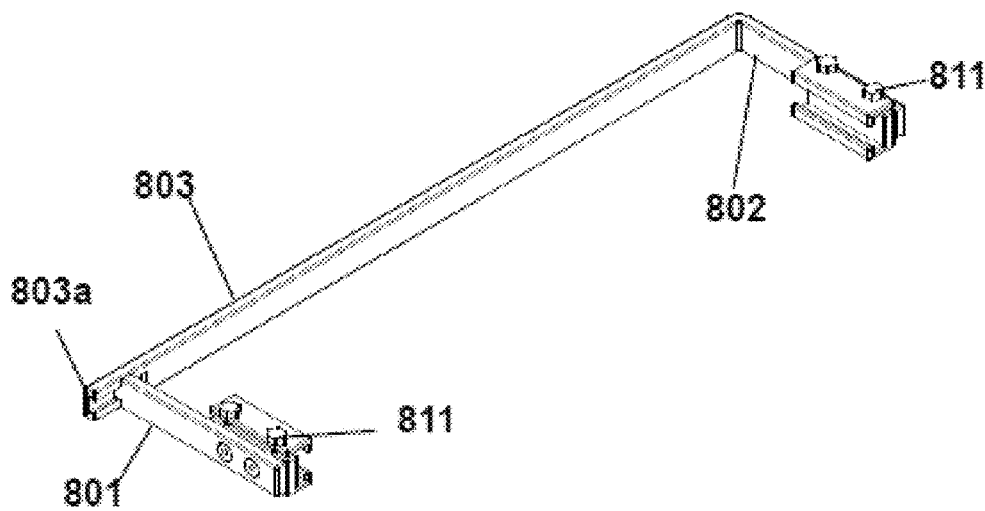
FIGS. 12A-12C show embodiments of an attachment wherein the length of an elongated body between a first arm and a second arm is adjustable.
Figure 12B:
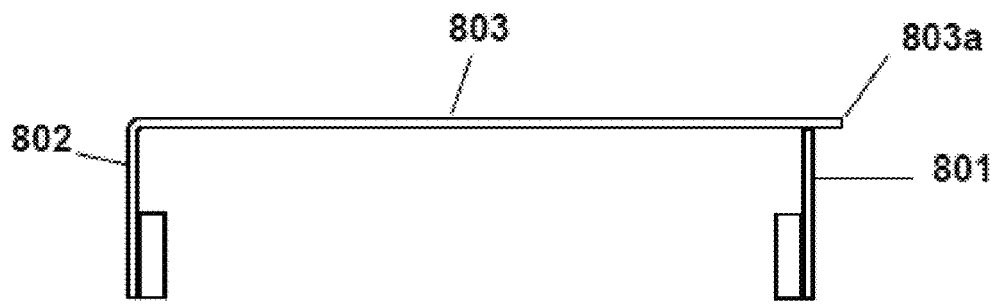
Figure 12C:
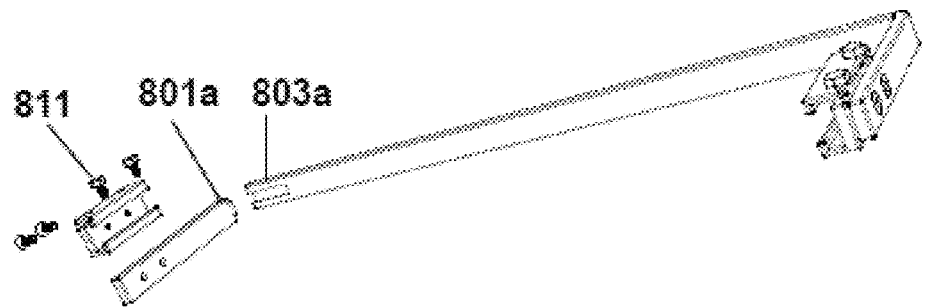

FIGS. 12A-12C show an embodiment of attachment 800 wherein the length of elongated body 803 between arm 801 and arm 802 is adjustable. FIG. 12A-C show a perspective view, top view and another perspective exploded view, respectively. FIG. 12A shows an embodiment wherein body 803 has a recessed or tracked end 803a configured receive a notched end 801a of arm 801, such that arm 801 may slide to a desired point along body 803. FIG. 12b shows a top view wherein arm 801 is maximally slid into body 803, and the length of body 803 between arm 801 and arm 802 is minimized. FIG. 12C shows an exploded view with components parts. One skilled in the art can appreciate there are various ways and adjustment mechanisms to adjust the length of body 803 with respect to arms 801 and 802. In other embodiments, body 803 may be detachable either arm 801 or 802, or from both arms.

FIGS. 13A-13D show perspective views of various embodiments of various sockets or caps 465 for a ball-and-socket rotational translator 470. FIG. 13A shows a simple cap 465. FIGS. 13B & 13C shows a cap with respective wide, curved and narrow sidewall slots 465a. FIG. 13D shows an inner textured surface 465b of cap 465. Textured surface 465b may be a variety of textures, such as concave or convex bumps to facilitate locking of the ball and socket when the ball 464 has corresponding convex or concave bumps respectively.

FIG. 13E shows an embodiment of sliding tube 491 and base 492, which may be compatible with a various embodiments of rotational translators 470. FIG. 13F shows an embodiment of threaded sliding tube 491 and base 492 configured for a screw designed vertical translator 490 and compatible with various embodiments of rotational translator 470. FIG. 13G shows an embodiment of outer texture surface 464b of cap 465. FIG. 13H shows an embodiment of outer surface of cap 465, wherein the outer surface of cap 464 is smooth.

FIGS. 13I and 13J show embodiments of a ball-and-socket rotational translator 470, wherein device coupler 430 is a non-threaded and threaded protrusion, respectively coupled to cap 465.

Figure 13K:
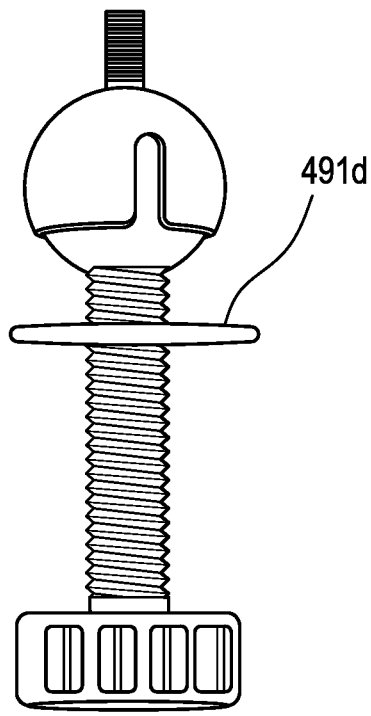
FIG. 13K shows an embodiment wherein a stem includes a washer or disk 491*d*.

FIG. 13K shows an embodiment wherein sliding tube 491 includes a washer or disk 491d configured to limit vertical translation of sliding tube 491. In embodiments, responsive to positioning disk 491d adjacent to couple portion 420, sliding tube 491 may no longer be vertically translated. FIG. 13L shows the embodiment within aperture 420h of stem's couple portion 420c. In this figure, disk 491d limits vertical translation of sliding tube 491 in a downward direction, wherein disk 491d may not be positioned below an upper surface of couple portion 420c. Disk 491d may be fixed along sliding tube 491 or may be a movable washer. FIG. 13M shows an embodiment wherein disk 491d is movable along sliding tube 491.

Figure 13N:
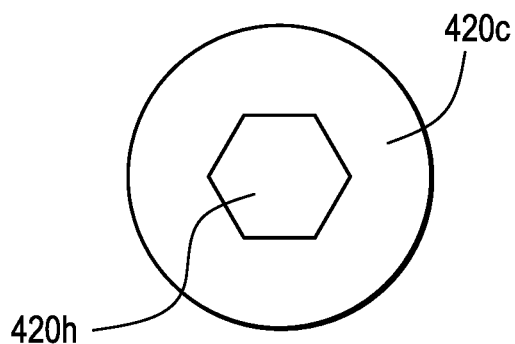
FIG. 13N is a cross sectional view of an aperture within the stem's coupling portion.
Figure 13L:
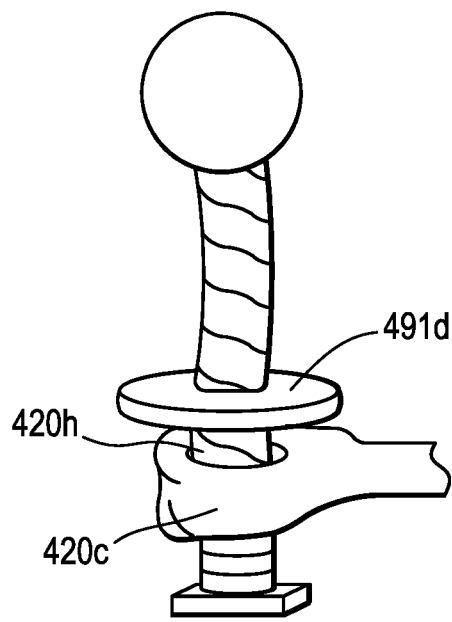
FIG. 13L shows the embodiment within an aperture of the stem's couple portion.
Figure 13M:
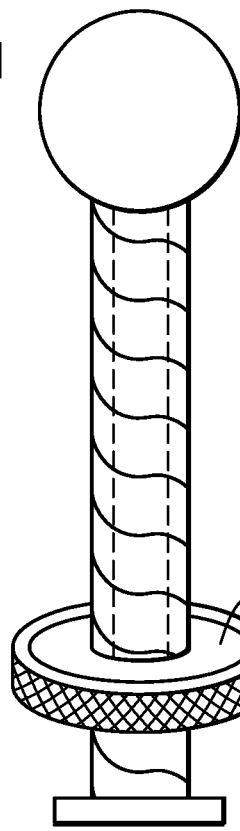
FIG. 13M shows an embodiment wherein a disk is movable along stem.

FIG. 13N is a cross sectional view of aperture 420h within stem's coupling portion 420c. Aperture 420h may have any polygonal or rounded shape configured to receive the shape of sliding tube 491. In this embodiment, aperture 420h is hexagonal, and configured to receive a hexagonal shaped and threaded sliding tube 491. This hexagonal shape has the benefit of creating additional resistance to prevent easy rotation of sliding tube 491 and undesired vertical translation of holder 400.

Figure 14A:
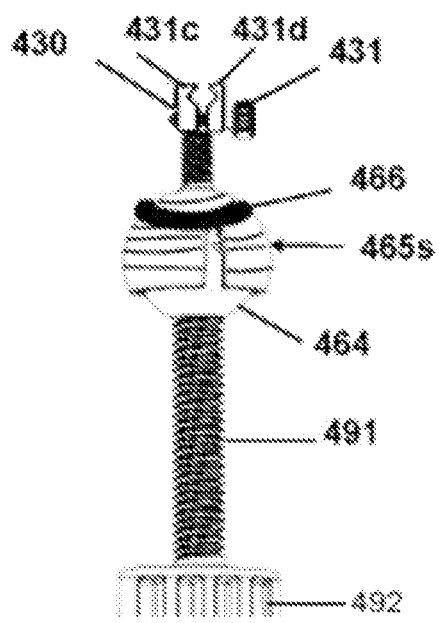
FIGS. 14A and 14B show alternative clamp embodiments of device coupler.
Figure 14B:
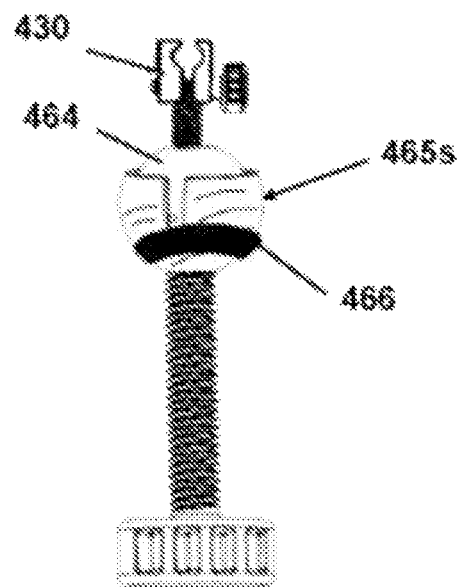

FIGS. 14A and 14B show alternative clamp embodiments of device coupler 430, wherein device coupler 430 is a clamp 431 configured to join or affix holder 400 to device 500. As shown in FIGURE A, clamp 431 may be coupled to a rotational translator 470 or a component thereof such as cap 465 (FIG. 14A) or ball 464 (FIG. 14B) to enable rotation of device 500. Clamp 431 may be separate or integral with cap 465 as shown in FIG. 14A, or ball 464 as shown in FIG. 14B. In embodiments, clamp 431 may also couple to another portion of holder 400, such as vertical translator 490, and/or or stem 420. Clamp 431 may affix any portion of device 500, and in particular a tubal portion. Clamp 431 may be substituted by any clasp, clip or grasping component.

Clamp 431 may be U V or O shaped. Clamp 431 may be comprised of two halves that open and close. Clamp 431 may include a tightening lock or screw portion 431a to secure device 500 and tighten the clamp. In the embodiment shown, screw portion 431a tightens a first half 431c with a second 431d and secure device 500. Clamp 431 may include any combination fasteners, bolts, clips, pins, latches, pegs, straps, locks, retaining rings, gully, fastening screws, or other coupling devices to fasten device 500.

Figure 14C:
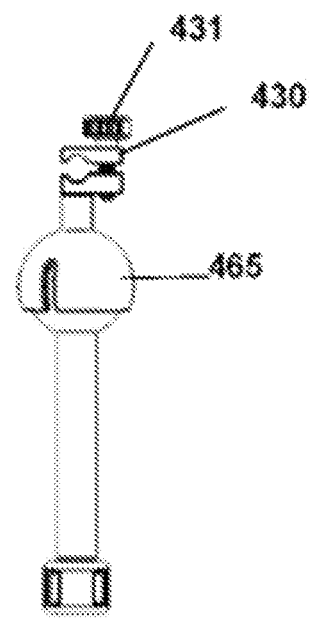
FIGS. 14C and 14D show embodiments of a clamp 431.
Figure 14D:
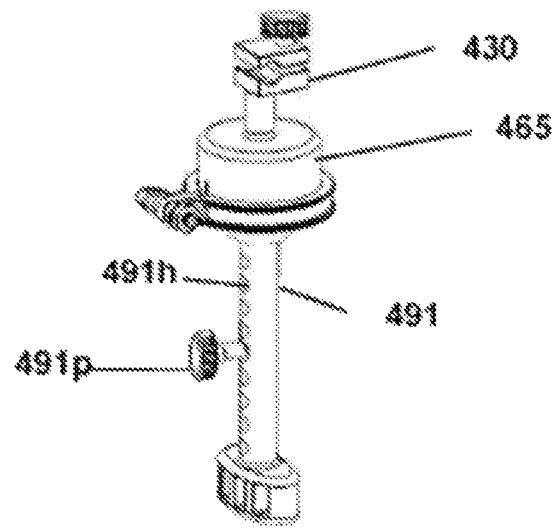

FIGS. 14C and 14D show embodiments where clamp 431 may be orientated to receive device 500 laterally as shown, in contrast to FIGS. 14A and 14B where the device 500 is orientated to receive device 500 vertically.

FIG. 14B shows an embodiment wherein the device coupler 430, and in particular clamp 431, is configured to couple to ball 464, instead of cap 465. The embodiment is advantageous wherein the cap is desired to be disposable.

FIGS. 14A and 14B show and embodiment where cap's surface 465A is textured or threaded. This embodiment may include, a ring 466 which may have corresponding or matching texture or threads on an inner surface. When twisted onto cap 465, ring 466 tightens cap 465 around ball 464 and thereby restricting rotational motion of ball 464, and by extension attached device coupler 430 and device 500. This may be desired after a particular rotational angle is achieved with device 500 and the practitioner seeks to lock the position into place. FIG. 14A shows the ring 466 may be positioned over cap 465 and may be twisted down onto cap 465 (when cap 465 is attached to a device coupler 430) for locking, whereas FIG. 14B shows that ring 466 may be positioned below cap 465 and may be twisted up vertically up onto the cap 465 (when ball 464 is coupled to device coupler 430) for locking.

Figure 15A:
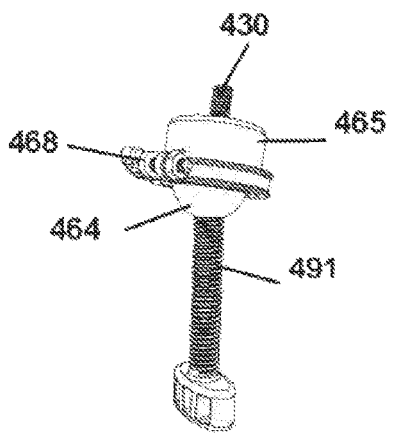
FIGS. 15A-F show an alternative embodiment of a rotational translator.
Figure 15B:
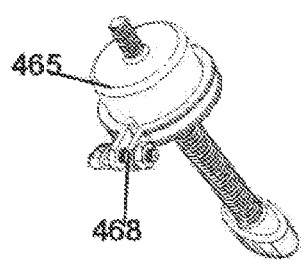
Figure 15C:
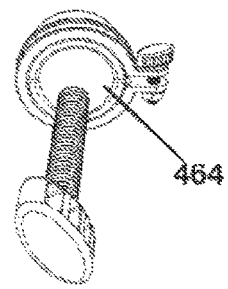
Figure 15D:
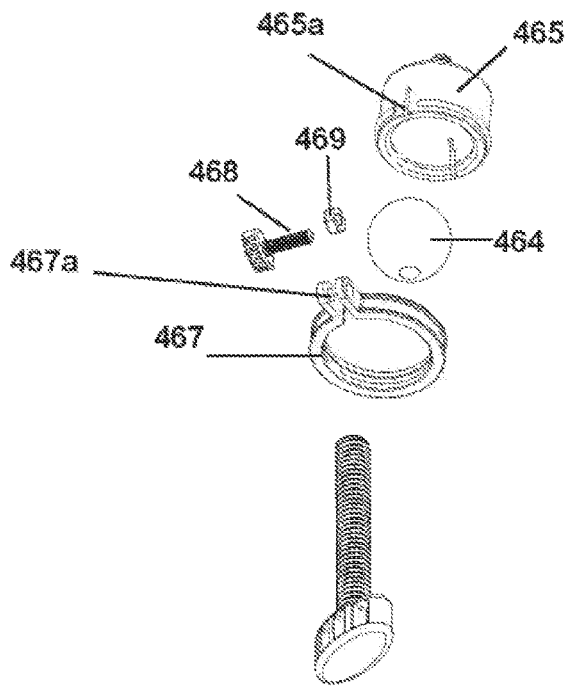
Figure 15E:
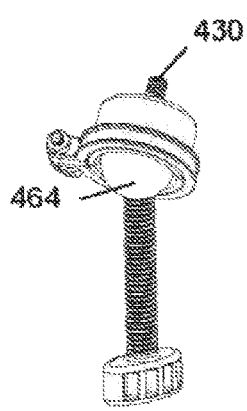

FIGS. 15A-F show an alternative embodiment of a rotational translator 470 comprised of a ball 464, cap 465, ring or hoop 467 with tightening screw 468 with an optional washer 469. FIGS. 15A-C show perspective views and 15D shows an exploded view. Hoop 467 is configured to couple to a surface, edge or rim of cap 465. Hoop 467 is discontinuous and has two apertures 467a to receive a tightening screw 468. Responsive to twisting tightening screw 468, a practitioner may lock in place the position of cap 465 relative to ball 464 and achieve a unique rotational angle, as shown in FIG. 15E.

Figure 15F:
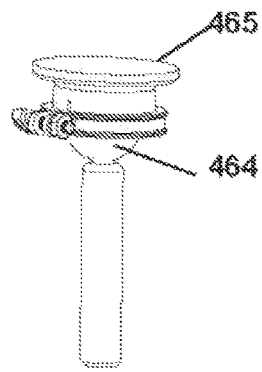

In this embodiment and other embodiments through the specification, threaded protrusion device coupler 430 is shown, however any device coupler embodiment such as a clamp 431 may be substituted. Similarly sliding tube 491 be threaded as a screw embodiment for a vertical translator 490, or may not be threaded and constitute one of the described embodiments (e.g., linear motion rail), as shown in FIG. 15F.

Figure 16A:
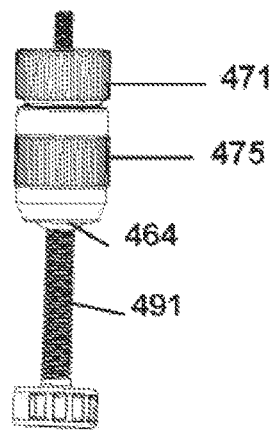
FIGS. 16A-D show an embodiment of a rotational translator.
Figure 16B:
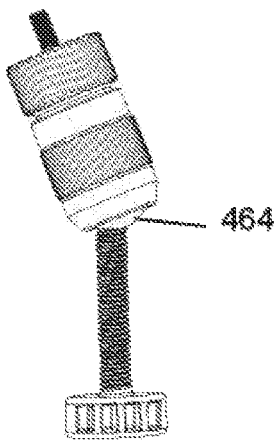
Figure 16C:
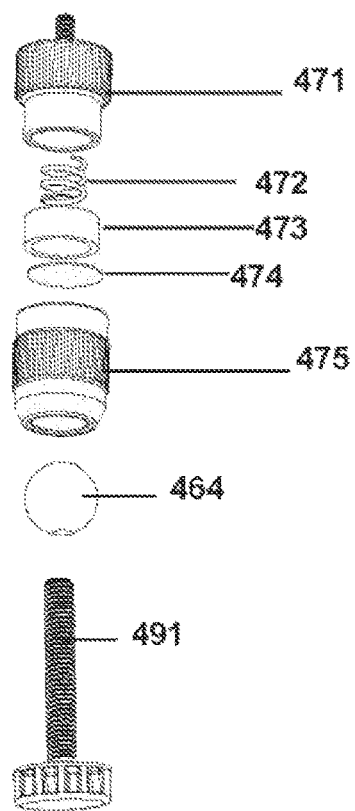
Figure 16D:
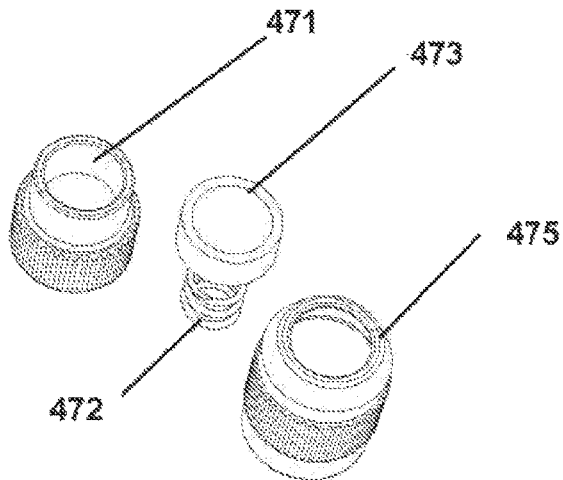

FIGS. 16A-D show an alternative embodiment of a rotational translator 470 showing a side perspective in FIG. 16A, a side perspective with the some amount of rotation in FIG. 16B, an exploded view in FIG. 16C, and specific elements in FIG. 16D. This embodiment is comprised of a twist cap 471, spring 472, spacer 473, optional disc 474, tightening ring 475, and ball 464. Ball 464 may be coupled to sliding tube 491 and positioned within tightening ring 475. Responsive to twisting tightening ring 474, ball 464 may be compressed by disk 474, spring 472, and spacer 473. Twist cap 471 may be configured to provide resistance to the spring 472, which may be configured to be positioned between spacer 473 and twist cap 471. Responsive to twisting tightening ring 474, ball 464 may be positioned into a fixed position by the forces applied by spacer 473 and tightening ring 475 against ball 464. Other embodiments may not include disk 474 and spring 472.

FIG. 17 shows an embodiment of flexible or adjustable gooseneck 405, which may be incorporated into holder 400 in various ways. Goosenecks are advantageous as they are malleable into any desired curved or straight orientation as the practitioner may prefer. In embodiments, sliding gooseneck's base platform 405p may be integral or part of plate 410 and/or attachment 800 and gooseneck 405 may be provide the desired rotational, vertical, longitudinal and lateral translation desired (with no other components other than coupling mechanisms). In yet other embodiments, gooseneck 405 may be coupled to various components of holders 400 described herein. For example, In embodiments, stem 420 may in part or whole be comprised of a gooseneck, and/or gooseneck base platform 405p may couple or be integral to carriage 455. In another embodiment, gooseneck 405 may substitute or comprise part of the vertical translator 490 or sliding tube 491 to achieve both vertical and rotational freedom. In yet another embodiment, gooseneck 491 may substitute or comprise part of the rotational translator 470.

In the embodiment shown, a first end of the gooseneck is coupled to a platform 405p and a second end is coupled to a device coupler 430, or clamp 431 in this embodiment. In other embodiments, gooseneck 405 may have a free-end not attached to a platform but rather some component of holder 400, and gooseneck's second end may attach to an alternative device coupler or some other components of holder 400 described herein.

For example, stem 420 may be flexible or adjustable with respect to it's length, height, or position. For example, stem 420 may have a gooseneck, so it is malleable into any desired curved or straight orientation as the physician may prefer, as shown in FIG. 17.

FIGS. 18-20 show embodiments of motion systems that may be incorporated in part or whole in the longitudinal translator 450, vertical translator 470 and lateral translator 480. These embodiments are for illustrative purposes to show the variety in motion systems and are non-exhaustive. FIGS. 18A-18C show respective perspective, side and bottom perspective views of a rail 454 configured for coupling with a ball bearing carriage 455. Rail 454 has a double barrel edge. Carriage 455 also includes a brake 458. Brake 458 may be a vertical stem or screw which is coupled to the bottom of carriage 455 and perpendicular to rail 454. Brake 458 may be configured to limit the motion of carriage 455 along rail 454. In other embodiments, brake 458 may be configured at any angle, and may couple to the side of carriage 455.

Figure 19A:
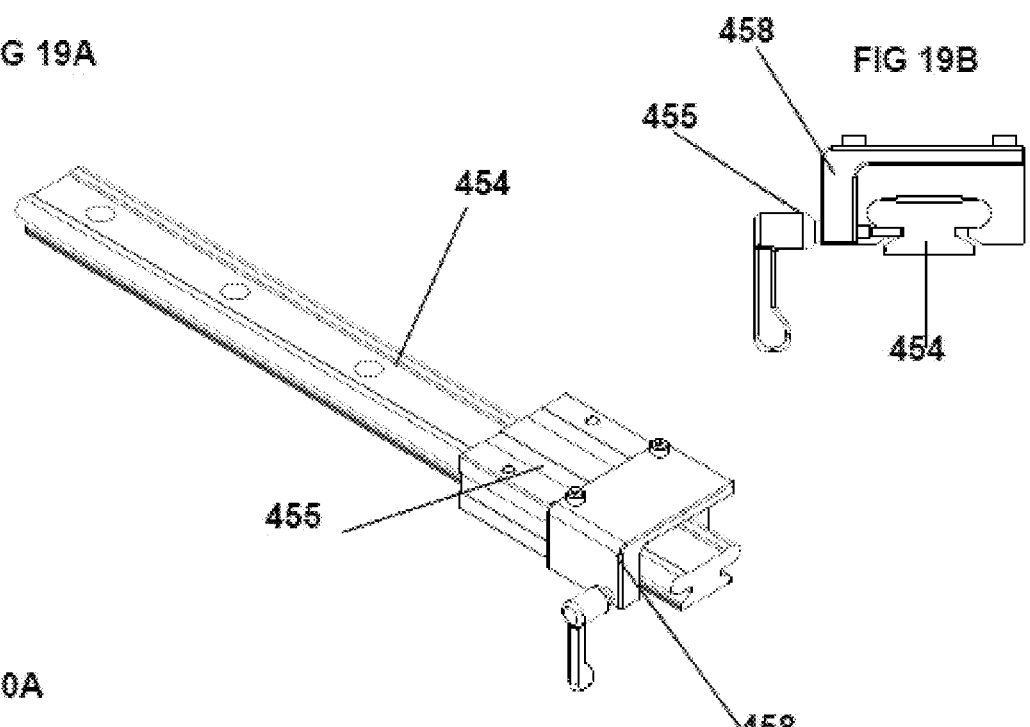
FIGS. 19A-B show perspective and side views of an embodiment where a brake is configured to be coupled to carriage.
Figure 19B:
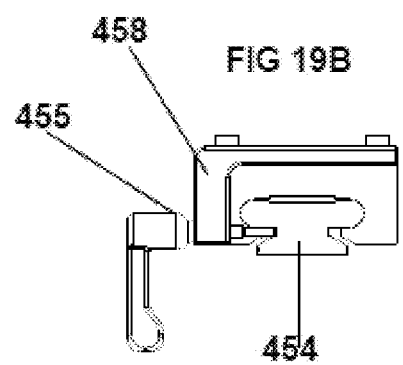

FIGS. 19A-B show perspective and side views of an embodiment where brake 458 is configured to be coupled to carriage 455. In embodiments, brake 458 may be a lever or clamp.

Figure 20A:
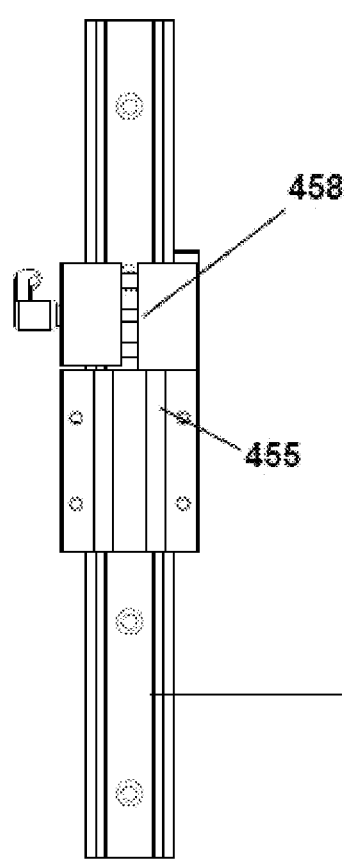
FIGS. 20A-B shows an embodiment where a break configured to be coupled to an end of a carriage.
Figure 20B:
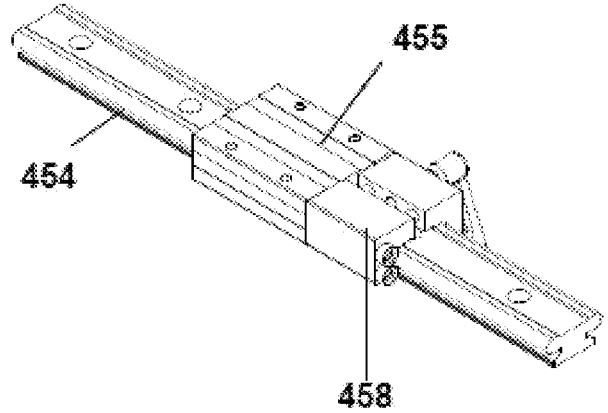

FIGS. 20A-B shows an embodiment where break 458 is configured to couple to an end of carriage 455 is has a clamping mechanism. The clamping mechanism may be configured to limit the motion of carriage 455 by increasing the friction caused by an inner surface of carriage 455 against rail 454. Any combination of parts of a motion system described or known may be combined to form the longitudinal translator 450, vertical translator 490, or when desired lateral translator 480.

Figure 21A:
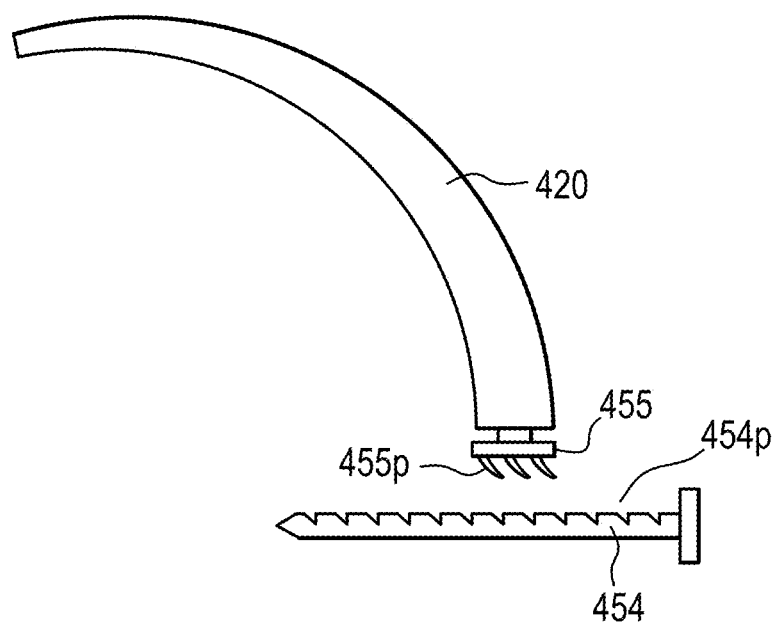
FIGS. 21A-B shows a side view of an embodiment of a longitudinal translator, and a perspective view of an embodiment longitudinal translator.

FIG. 21A shows a side view of an embodiment of a longitudinal translator 450 wherein carriage 455 is configured with protrusions, teeth, notches, or pins 455p and rail 454 is configured with a series of indentations, gullies, tranches, indentations, or valleys 454p such that when pins 455p translates along track 454, pins 455 may lock into a valley 454p. Carriage 455 may be spring-loaded such that responsive to pushing or pressing stem 420 down, carriage 455 is lifting off rail and pins 455p disengages from valleys 454p on rail 454 to allow translation. Without downward pressure, stem 420 may be fixed into position via one more pins 455p locked into valley 454p.

Figure 21B:
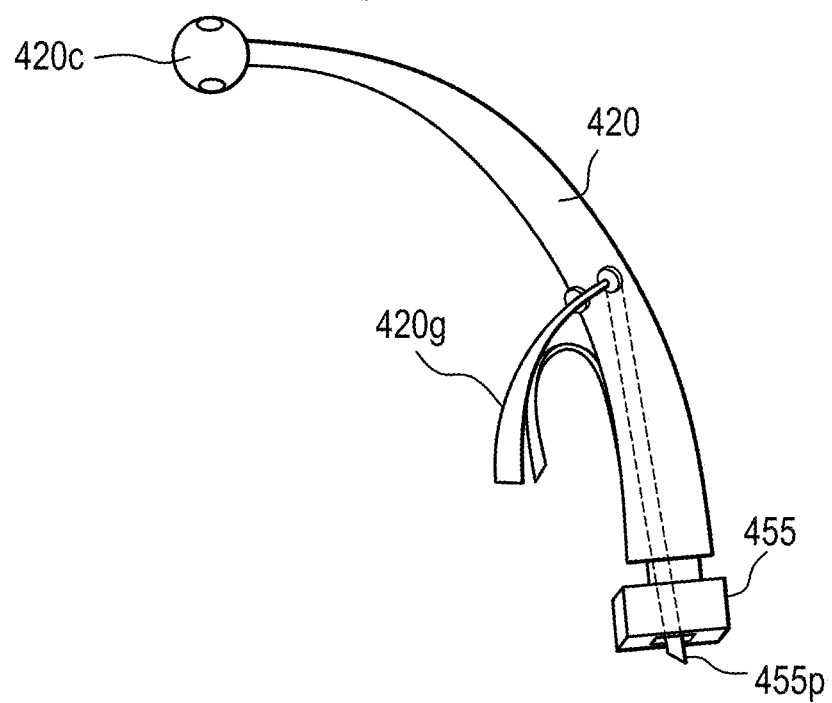

FIG. 21B shows a perspective view of an embodiment longitudinal translator 450 wherein carriage 455 is spring-loaded to allow vertical movement of pin 455p and engagement and disengagement from valleys 454p on rail 454. FIG. 21B also shows a spring actuator 420g attached to stem 420 for ergonomic handling, wherein when pressed actuator 420g may release pin 455p from the rail 454 to allow translation of carriage 455 along rail 454, or alternatively may drop pin 455p into rail 454 to prevent movement. FIG. 21B also shows a spherical ball embodiment of coupling portion 420c, which may be alternative shapes and sizes.

FIG. 21C shows a side perspective view of an embodiment longitudinal translator 450 wherein carriage 455 is spring-loaded with actuator 420g to enable engagement and release of pin 455p into and from rail 454. FIG. 21D shows a top view of rail 454 with a series of valleys 454p.

FIG. 21E shows a side view of an embodiment wherein pin 455p is spring-loaded via a spring pin or spring 455s. FIG. 21F shows a perspective view of FIG. 21E. Spring 455s may be coupled to stem 420 or carriage 455, or some combination of both.

FIG. 21G shows alternative embodiment of spring 455s wherein spring 455s is a tension spring and coupled to stem 420.

Figure 22:
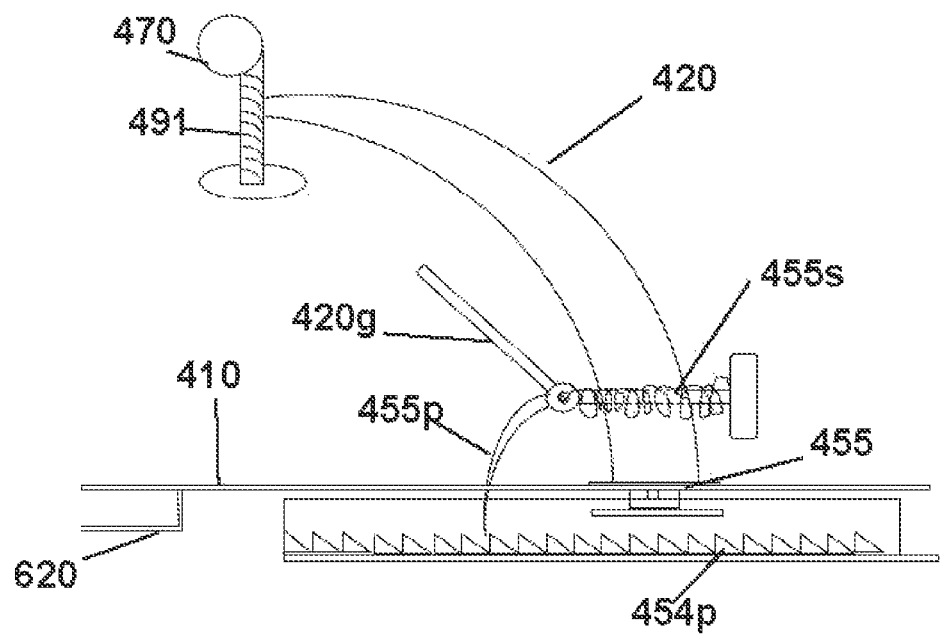
FIG. 22 shows a side view of an embodiment a pin braking carriage.

FIG. 22 shows a side view of an embodiment wherein holder 400 is configured with plate 410 and track's base 444 includes valleys 454p to receive pin 455p for braking or locking carriage 455. In this embodiment, braking pin 455p is coupled or configured with actuator 420g on stem 420 such that when actuator 420g is lifted (for example by an index finger of a hand wrapped around stem 420), pin 455s is lifted and released from track 444 and valleys 454p allowing free movement of the carriage 455. Actuator 420g and pin 455s may be coupled with a spring 455s to generate a spring force or resistance.

Figure 23:
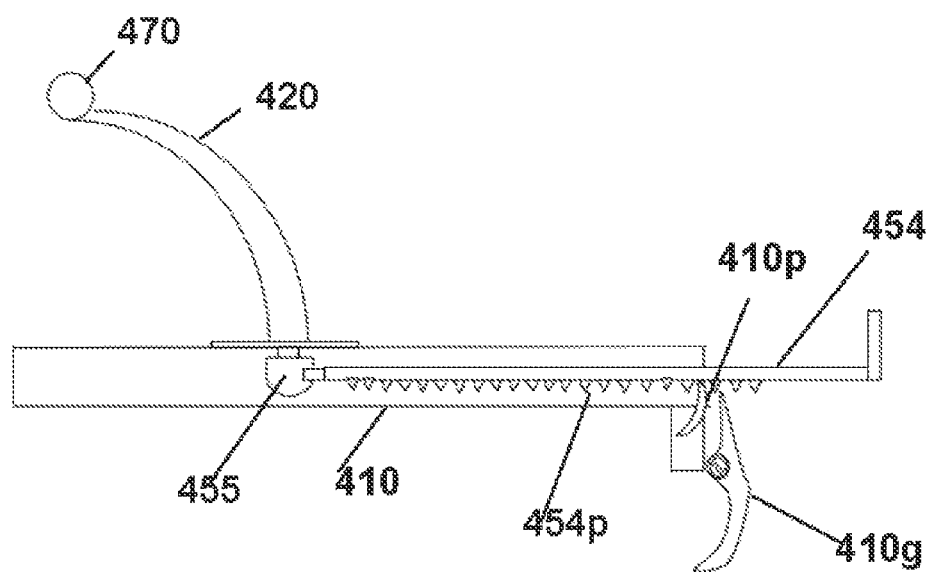
FIG. 23 shows a side view of an embodiment of a holder with a pin braking system.

FIG. 23 shows a side view of another embodiment of holder 400 wherein rail 454 is coupled to carriage 455, so when rail 454 moves, carriage 455 correspondingly moves. In embodiments, carriage 455 may be configured to couple to a ball or wheel which slides along a track 444 of plate 410. Alternatively, carriage 455 may slide on plate 410. In another embodiment, carriage 455 slides along a second rail, rather than plate 410, while rail 454 translates carriage 455 along the second rail.

FIG. 23's translation system is similar to "caulking gun", whereupon triggering actuator 410g, rail 454 advances a notch and a valley 454p moves from the proximal side of pin 410p to the distal side of pin 410p. Pin 410p prevents reverse translation of valley 454p, and by extension rail 454. A practitioner may rotate rail 454 so pin 410p disengages from valley 454p and achieve free translation of rail 454. Practitioner may rotate the valleys 454p back into pin 410p to lock rail 454 into place and achieve the desired positioning/longitudinal translation.

Figure 24:
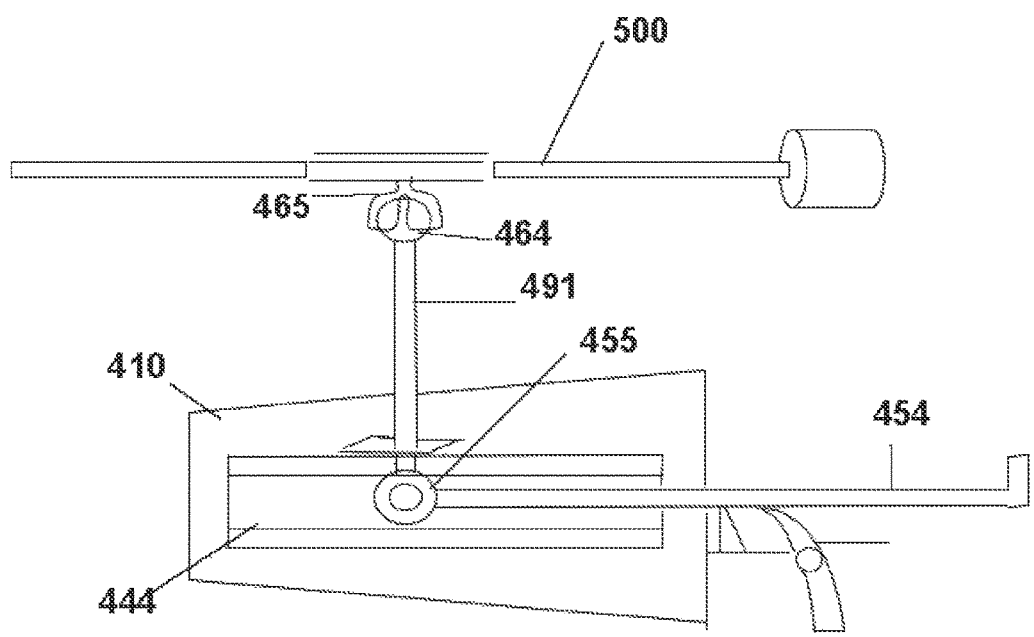
FIG. 24 shows a side view of an embodiment of a holder without a vertical translator.

IN FIG. 24, rail 454 has a similar "caulking" translation system described in the previous embodiment, FIG. 23. In the embodiment shown, rail 454 has a series of valleys 454p. Plate's first end 410a has an actuator 410g, so when rail 454 moves, carriage 455 correspondingly moves. Carriage 455 is configured to couple to a ball or wheel which slides along a track 444 of plate 410. However, vertical translator 490 is absent; thus in this embodiment, holder may only translate longitudinally and rotationally.

Figure 25:
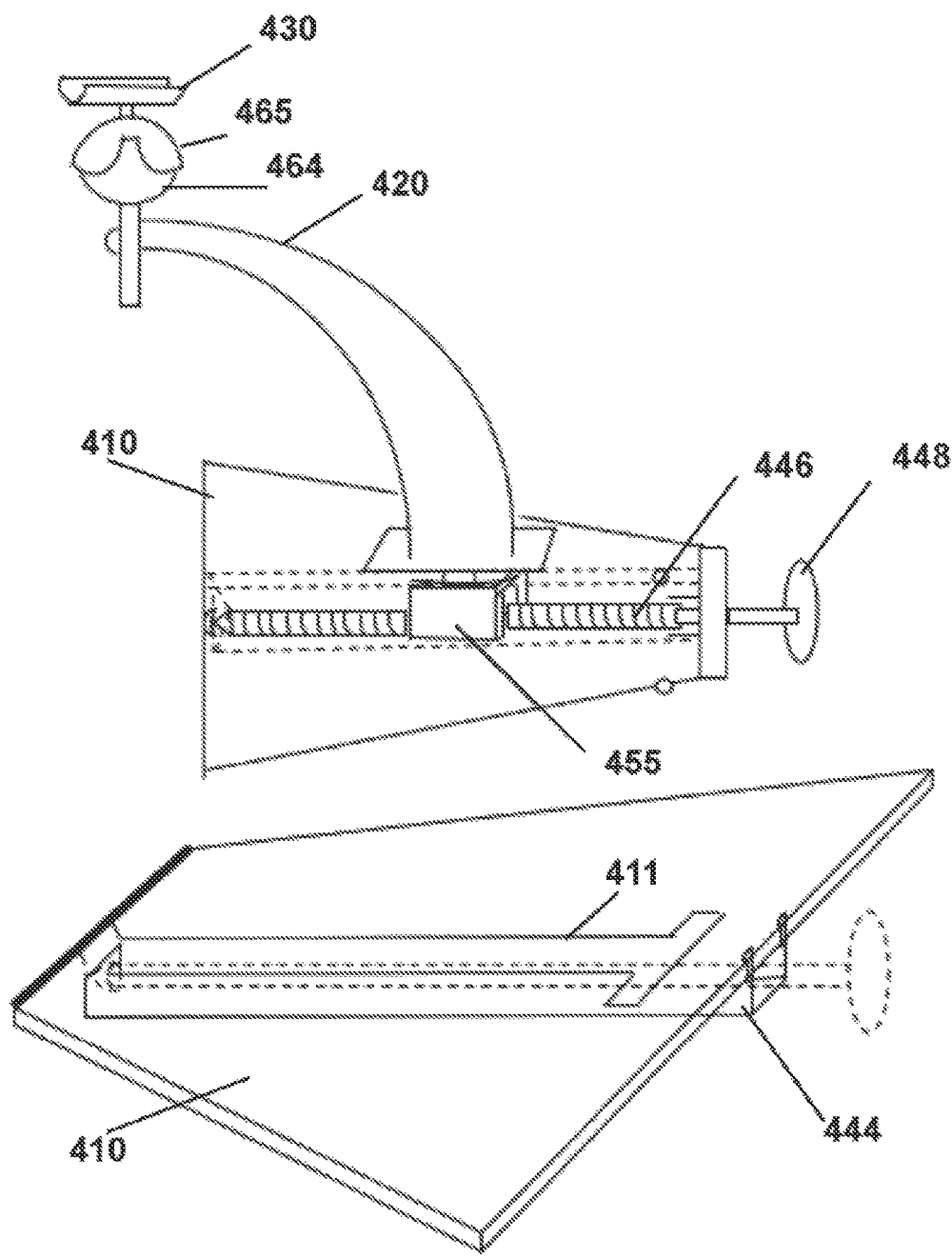
FIG. 25 shows a perspective view of a half-bolt embodiment of a longitudinal translator.

FIG. 25 shows a perspective view of another embodiment of holder 400. Handle 454h may be configured as a bolt or half bolt, wherein the gripping portion 448 remains outside of the plate for pulling and pushing, and an extended half bolt, screw, or length portion 446 is coupled to or passes through carriage 455. Half bolt 446 may be coupled to a fixed point along longitudinal translator. Accordingly, when carriage 455 moves, half bolt 446 may correspondingly move. For example, responsive to carriage 455 moving in the first direction, half bolt 446 may move in the first direction.

Gripping portion 448 may be an interface that extends away from the first end of Plate 410, wherein a physician may interact with handle 448. For example, handle 448 may be a twist handle configured to receive rotational force, a button or switch configured to robotically, mechanically, etc. move carriage 455.

Responsive to the physician interacting with handle 448, carriage 455 may move between the first end and second end of the base plate. In an embodiment, responsive to a physician rotating handle 448 in a first direction, carriage 455 may move along the linear path in a first direction, wherein the first direction is from the first end of Plate 410 towards the second end of Plate 410. Responsive to the physician rotating handle 448 in a second direction, carriage 455 may move along the linear path in a second direction, wherein the second direction is from the second end of Plate 410 towards the first end of Plate 410.

Furthermore, responsive to the physician interacting with handle 448, handle 448 may lock carriage 455 in place in a fixed position. One skilled in the art will appreciate that handle 448 may instead also be buttons, electrical switches, etc. being configured to mechanically, electrically, or robotically move longitudinal translator 450 in the first and second directions responsive to the physician interfacing with the buttons.

Figure 26:
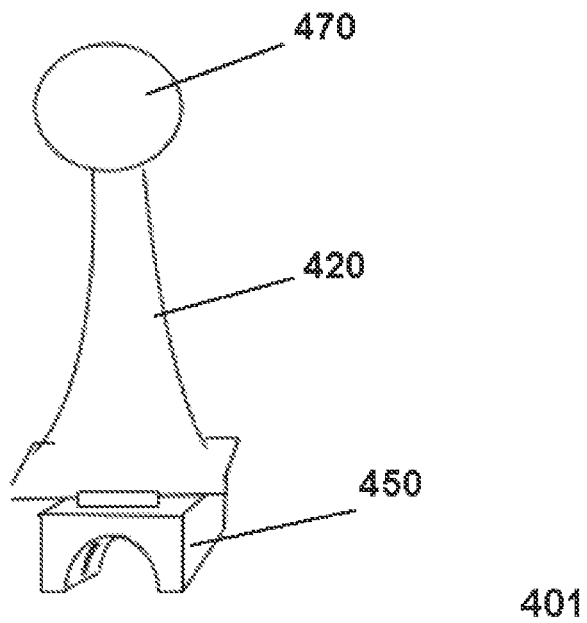
FIG. 26 shows an embodiment of a ball bearing carriage

FIG. 26 shows an embodiment of a ball bearing carriage 450 coupled with stem 420 and rotational translator 470.

FIG. 27 illustrates an embodiment wherein attachment 800 and plate 410 are combined to form a hybrid attachment to base 200. In this embodiment plate 410 has two arm attachments 401 and 402 which attach or couple plate 410 to base 100 by bolts 211.

In using the holder, practitioner may couple the device to the device coupler, adjust the vertical translator to reach the vaginal introitius height appropriately, slide the longitudinal slide to achieve the appropriate distance from the patient or appropriate force applied against the patient, and rotate the rotational translator to achieve the desired angle.

When medical device is a uterine manipulator, a lateral translator may optionally be used throughout a procedure to achieve lateral translation of an organ, such as a uterus. The longitudinal translator may achieve retracting or pushing forward a uterus. And the rotational translator may achieve achieving rotations or a particular angle of the medical device within the uterus of the patient. Vertical translation may enable elevation of the uterus. These translations and six degrees of freedom facilitate a hysterectomy.

The operations of method 1400 presented below are intended to be illustrative. In some embodiments, method 1400 may be accomplished with one or more additional operations not described, and/or without one or more of the operations discussed.

At operation 1410, a track may be coupled to a platform, wherein the track may be positioned within a cavity at a first end of the platform. The platform may be coupled to the platform via a plate, mechanical arms, and/or any other coupling mechanism.

At operation 1420, a stem of a manipulator holder may slide along a linear path defined by the track. The stem may slide between a first end of the track and second end of the track.

At operation 1430, the stem of the manipulator holder may be secured at a fixed positioned within the track.

At operation 1440, the manipulator holder may be rotated and adjusted to any desired position. The manipulator holder may be moved, such that when a physician is performing a hysterectomy or other surgical procedures on a woman, the patient's uterus may be manipulated. By manipulating the patient's uterus, the physician may view the uterus and cervix properly.

One skilled in the art can appreciate that any or all components or parts described herein may be configured for motor, electronic, magnetic, or automatic control. For example, longitudinal translator 450, vertical translation 490, rotational translator 470, or lateral translator 480 or any of its components may have couplings to enable electronic instead of mechanical operation.

Various embodiments of a holder are described throughout this specification which include some or all elements of a vertical translator 490, rotational translator 470, longitudinal translator 450, and lateral translator 480. Embodiments of a holder may be comprised of one or more of these translators (and ranges of motion) to comprise a holder 400. Holder 400 may also be attached to a plate 410 or attachment 800, or any combination thereof. Thus, embodiments need to require 6 degrees of freedom, but may accomplish less. Additionally, components throughout these various embodiments may be substituted into other embodiments. In addition, when vertical translator 490, longitudinal translator 450, or lateral translator 480 are configured as a linear motion system, either translator may incorporate features of another embodiment of another linear motion translator described or referenced in this specification.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

Reference throughout this specification to "one embodiment", "an embodiment", "one example" or "an example" means that a particular feature, structure or characteristic described in connection with the embodiment or example is included in at least one embodiment of the present invention. Thus, appearances of the phrases "in one embodiment", "in an embodiment", "one example" or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

The invention claimed is:

1. A medical device holder comprising:
 a rail;
 a carriage configured to attach and move relative to the rail, together comprising a linear motion system;
 a stem with a first end and a second free end, wherein the first end is coupled to the linear motion system to enable linear motion of the stem along a first axis in parallel to a surface of an operating table, and the second free end is configured to enable vertical movement of a medical device in a second axis, the second axis being perpendicular to the first axis;
 an attachment with an elongated body, a first arm, and a second arm, wherein the first arm couples with a first side of the operating table, the second arm couples with a second side of the operating table, and the elongated body extends from the first arm to the second arm in a direction perpendicular to the first arm and the second arm.

2. The medical device holder of claim 1, wherein a length of the elongated body is adjustable.

3. The medical device holder of claim 1, wherein a first end of the elongated body includes a first end carriage coupled to the first arm and a second end of the elongated body includes a second end carriage coupled to the second arm; wherein the carriage is configured for lateral translation along the elongated body, and wherein the elongated body is configured for longitudinal translation along the first arm and second arm via the first end carriage and the second end carriage.

4. The medical device holder of claim 1, wherein the stem's second free end is coupled to a vertical translator, the vertical translator being configured to couple with the medical device and to adjust a vertical offset of the medical device from the carriage.

5. The medical device holder of claim 4, wherein the vertical translator includes a screw, a threaded connection portion, and a base portion, wherein responsive to the base portion being rotated to screw vertically moves through the threaded connection portion to change the vertical offset of the device.

6. The medical device holder of claim 4, wherein the vertical translator is coupled to a rotational translator, the rotational translator being configured to couple with the medical device and allow the medical device to be angularly rotated in a plurality of directions and angles.

7. The medical device holder of claim 1, wherein the medical device is configured to couple to a rotational translator, the rotational translator being configured to allow the medical device to be angularly rotated in a plurality of directions and angles.

8. The medical device holder of claim 7, wherein the rotational translator is comprised of a ball and a cap.

9. The medical device holder of claim 8, wherein the ball or cap is detachable.

10. The medical device holder of claim 8, wherein the ball and the cap have a locking mechanism to fix the position of the ball relative to the cap.

11. The medical device holder of claim 8, wherein a portion of the rotational translator includes a threaded protrusion, wherein the threaded protrusion is configured for coupling or screwing into the medical device.

12. The medical device holder of claim 7, wherein a portion of the rotational translator is coupled to a clamp configured to fasten the medical device to the holder.

13. The medical device holder of claim 1, wherein the carriage includes a brake or a clamp to stop motion of the carriage relative to the rail.

14. The medical device holder of claim 1, wherein the stem is configured as an arch.

15. The medical device holder of claim 1, wherein the stem is detachable from the linear motion system.

16. The medical device holder of claim 1, wherein the stem's second free end includes an aperture for receiving a tube.

17. The medical device holder of claim 16, wherein the tube is threaded, and an inner surface of the aperture has a threaded surface that corresponds to the threads on the tube.

18. The medical device holder of claim 17, wherein the aperture is configured for receiving a pin or screw.

19. The medical device holder of claim 17, wherein a second linear motion system includes the tube and the aperture, and wherein a braking mechanism is attached to the aperture to lock the tube into position.

* * * * *